United States Patent
Sunderland

(10) Patent No.: US 10,111,622 B2
(45) Date of Patent: Oct. 30, 2018

(54) EVALUATION OF THE QUALITY OF ELECTRODE CONTACT WITH A SKIN SURFACE

(71) Applicant: Welch Allyn, Inc., Skaneateles Falls, NY (US)

(72) Inventor: Richard A. Sunderland, Aloha, OR (US)

(73) Assignee: WELCH ALLYN, INC., Skaneateles Falls, NY (US)

( * ) Notice: Subject to any disclaimer, the term of this patent is extended or adjusted under 35 U.S.C. 154(b) by 0 days.

(21) Appl. No.: 15/379,080

(22) Filed: Dec. 14, 2016

(65) Prior Publication Data

US 2017/0086744 A1 Mar. 30, 2017

Related U.S. Application Data

(60) Continuation of application No. 14/996,320, filed on Jan. 15, 2016, now Pat. No. 9,554,749, which is a division of application No. 14/269,933, filed on May 5, 2014, now Pat. No. 9,271,659, which is a division
(Continued)

(51) Int. Cl.
| | |
|---|---|
| *A61B 5/04* | (2006.01) |
| *A61B 5/00* | (2006.01) |
| *A61B 5/0478* | (2006.01) |
| *A61B 5/0492* | (2006.01) |
| *A61B 5/0424* | (2006.01) |
| *A61B 5/0408* | (2006.01) |
| *A61B 5/053* | (2006.01) |
| *A61B 5/0428* | (2006.01) |

(52) U.S. Cl.
CPC .......... *A61B 5/6843* (2013.01); *A61B 5/0424* (2013.01); *A61B 5/0478* (2013.01); *A61B 5/04085* (2013.01); *A61B 5/0492* (2013.01); *A61B 5/04286* (2013.01); *A61B 5/053* (2013.01); *A61B 5/742* (2013.01)

(58) Field of Classification Search
None
See application file for complete search history.

(56) References Cited

U.S. PATENT DOCUMENTS

| | | |
|---|---|---|
| 4,577,639 A | 3/1986 | Simon et al. |
| 5,879,308 A | 3/1999 | Raesaenen et al. |
| 6,377,845 B1 | 4/2002 | Kinast |

(Continued)

FOREIGN PATENT DOCUMENTS

| | | |
|---|---|---|
| EP | 1432349 B1 | 6/2006 |
| WO | 2010129026 A2 | 11/2010 |

OTHER PUBLICATIONS

Baba et al., "Measurement of the Electrical Properties of Ungelled ECG Electrodes," International Journal of Biology and Biomedical Engineering, Issue 3, vol. 2, 2008, 9 pages.
(Continued)

*Primary Examiner* — Ankit D Tejani
(74) *Attorney, Agent, or Firm* — Merchant & Gould P.C.

(57) ABSTRACT

An instrument that utilizes body contact electrodes evaluates the quality of the connections made between the electrodes and the body. An electrode contact quality evaluation circuit performs the quality evaluation, such as by determining contact impedances for the electrodes. The corresponding contact quality of each electrode is conveyed to the user.

3 Claims, 15 Drawing Sheets

Related U.S. Application Data of application No. 13/624,645, filed on Sep. 21, 2012, now Pat. No. 8,755,873.

(56)  References Cited

U.S. PATENT DOCUMENTS

| | | |
|---|---|---|
| 6,496,721 B1 | 12/2002 | Yonce |
| 6,602,201 B1 | 8/2003 | Hepp et al. |
| 7,818,058 B2 | 10/2010 | Mentelos |
| 2002/0107435 A1 | 8/2002 | Swetlik |
| 2003/0032989 A1 | 2/2003 | Herleikson |
| 2007/0038257 A1 | 2/2007 | Gray |
| 2007/0073175 A1 | 3/2007 | McAtamney |
| 2008/0275316 A1 | 11/2008 | Fink et al. |
| 2008/0281168 A1 | 11/2008 | Gibson et al. |
| 2009/0259137 A1 | 10/2009 | Delic |
| 2010/0007413 A1 | 1/2010 | Herleikson |
| 2011/0092834 A1 | 4/2011 | Yazicioglu et al. |
| 2011/0208183 A1 | 8/2011 | Stockert |
| 2011/0213261 A1 | 9/2011 | Naware et al. |
| 2012/0065536 A1* | 3/2012 | Causevic ........... A61B 5/04004 600/544 |
| 2012/0209086 A1 | 8/2012 | Beute |

OTHER PUBLICATIONS

Degen et al., "Continuous Monitoring of Electrode-Skin Impedance Mismatch During Bioelectric Recordings," IEEE Transactions on Biomedical Engineering, vol. 55, No. 6, Jun. 2008, 5 pages.

Grimbergen et al., "A Method for the Measurement of the Properties of Individual Electrode-Skin Interfaces and the Implications of the Electrode Properties for Preamplifier Design," IEEE copyright Feb. 1992, 2 pages.

Grimnes, S., "Impedance Measurement of Individual Skin Surface Electrodes," Medical & Biological Engineering & Computing, Nov. 1983, 6 pages.

Spach et al., "Skin-Electrode Impedance and Its Effect on Recording Cardiac Potentials," Circulation Journal of the American Heart Association, copyright 1966, 9 pages.

PCT International Searching Authority, International Search Report and Written Opinion for International Application No. PCT/US2013/060114 dated Dec. 27, 2013, 10 pages.

* cited by examiner

EVALUATION OF THE QUALITY OF ELECTRODE CONTACT WITH A SKIN SURFACE

CROSS REFERENCE TO RELATED APPLICATION

This application is a continuation of U.S. patent application Ser. No. 14/996,320, filed on Jan. 15, 2016, entitled EVALUATION OF THE QUALITY OF ELECTRODE CONTACT WITH A SKIN SURFACE, which is a divisional of U.S. Pat. No. 9,271,659, filed on May 5, 2014, entitled EVALUATION OF THE QUALITY OF ELECTRODE CONTACT WITH A SKIN SURFACE, which is a divisional of U.S. Pat. No. 8,755,873, filed on Sep. 21, 2012, entitled EVALUATION OF THE QUALITY OF ELECTRODE CONTACT WITH A SKIN SURFACE, the disclosures of which are hereby incorporated by reference in their entireties.

BACKGROUND

There are a variety of instruments that are designed to interact with a patient through electrodes applied to the patient's skin. Several examples include electrocardiograph (ECG), electroencephalograph (EEG), and electromyograph (EMG) instruments. Such instruments operate by making electrical connections with the skin, through which electrical signals can pass.

The quality of the contact between the electrode and the skin can greatly impact the quality of the signal obtained from the patient. Several factors can influence the quality of the connection. A major factor is whether appropriate skin preparation steps are taken prior to the connection of the electrode. A skin preparation process may include shaving the skin surface to remove hairs, cleaning the skin surface, and lightly abrading the skin surface to remove dead skin cells. The electrode itself can also influence the quality of the connection. For example, some types of electrodes can become dried out over time. The electrical connection quality can also be reduced if a conductive gel is not applied between the skin and certain types of electrodes that require such a gel. If a non-conductive gel, such as a type used for ultrasound procedures, is inadvertently used, the quality of the electrical connection can be reduced.

Even if electrodes appear to be well connected to the skin and skin preparation has been properly done, the quality of the electrical contact can still be relatively poor for some patients. A visual or physical inspection of the electrodes is not adequate to determine the quality of the connection. A poor electrical connection can result in increased susceptibility to interference, or complete inability of the instrument to interact with the patient in the intended manner.

SUMMARY

In general terms, this disclosure is directed to systems and methods for evaluating the quality of electrode contact with a skin surface.

One aspect is an instrument comprising: a lead interface device configured to electrically communicate with at least three surface contact electrodes; instrument electronics configured to detect electrical signals from the surface contact electrodes; and electrode contact quality evaluation circuitry operable to determine a quality of electrical connections between the surface contact electrodes and a skin surface.

Another aspect is an electrode contact quality evaluation device configured to evaluate a connection between at least one electrode and a skin surface, the electrode contact quality evaluation device comprising: a current source that generates a test current; an injection electrode selection circuit that supplies the test current to a selected injection electrode through a selected injection lead; a driven return circuit that generates a return current having opposite polarity to the test current; a return electrode selection circuit that supplies the return current to a selected return electrode through a selected return lead; a sense electrode selection circuit that supplies a signal obtained from one or more selected sense electrodes through one or more selected sense leads, to the driven return circuit; differential measurement circuitry that measures differences between signals present at the injection lead and the one or more sense leads and between signals present at the one or more sense leads and the return lead; and a processing device that evaluates the differences and generates an output representing a quality of at least one connection between at least one of the electrodes and the skin surface.

A further aspect is an electrocardiograph comprising: a base unit comprising: a housing; a computing device at least partially contained within the housing; and an output device at least partially contained within the housing and configured to output information associated with electrical signals from the heart of a patient detected by the electrocardiograph; a lead interface unit having a lead interface housing separate from the housing of the base unit, the lead interface unit comprising: a lead interface arranged and configured to physically connect the lead interface unit to electrically conductive leads, wherein the leads are configured to be physically connected to surface contact electrodes; electrode contact detection circuitry within the lead interface housing that detects contact between the surface contact electrodes and the patient; electrode contact quality evaluation circuitry within the lead interface housing, wherein the electrode contact quality evaluation circuitry determines a quality of electrical connections between the surface contact electrodes and the patient; and instrument electronics within the lead interface housing that detect electrical signals from the heart of the patient; and a communication interface between the lead interface unit and the base unit.

Yet another aspect is a method of evaluating the quality of electrode contact with a skin surface, the method comprising: checking for and determining that at least three electrodes are in physical contact with a skin surface using electrode contact detection circuitry; and evaluating and determine a quality of an electrical connection between at least one of the electrodes and the skin surface using electrode contact quality evaluation circuitry.

DETAILED DESCRIPTION

Figure 1:
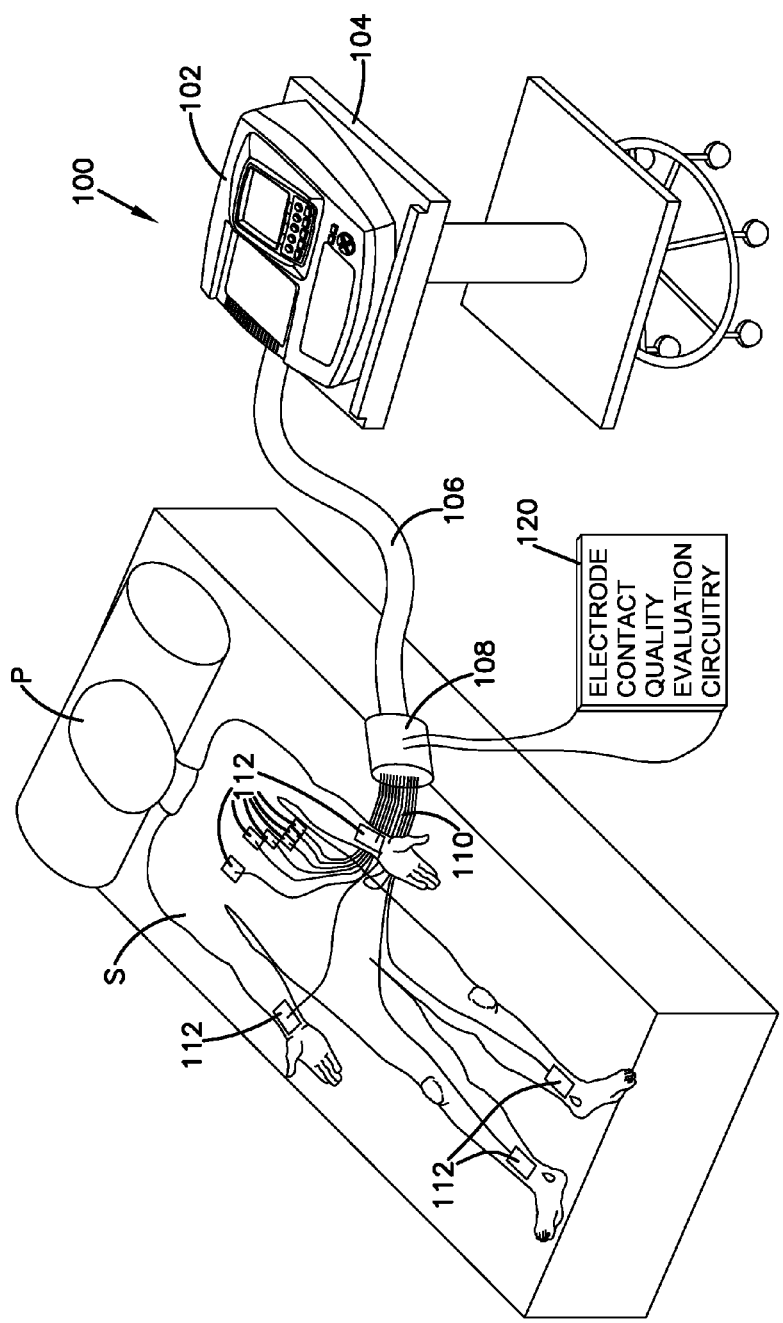
FIG. 1 is a perspective view of an example instrument that interacts with a patient through surface contact electrodes.

Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

FIG. 1 is a perspective view of an example instrument 100 that interacts with a patient through skin contact electrodes. The instrument 100 can take various forms in a variety of possible embodiments. Several examples of the instrument 100 include an electrocardiograph (ECG), an electroencephalograph (EEG), and an electromyograph (EMG) instrument. The following description makes reference to an example embodiment involving an electrocardiograph instrument 100, but it is recognized that other embodiments include other instruments in which skin contact electrodes are used to interact with a patient.

In this example, the instrument 100 is a mobile electrocardiograph instrument that includes a base unit 102, a cart 104, a cable 106, a lead interface unit 108, leads 110, and electrodes 112. The electrical components of the instrument 100 are contained within the base unit 102 and the lead interface unit 108. The cart 104 provides a mobile platform that supports the base unit 102. The cable 106 and leads 110 include electrical conductors which conduct electrical signals between the base unit 102, the lead interface unit 108, and the electrodes 112. The electrodes 112 are connected to the skin S of the patient P.

The electrocardiograph instrument 100 utilizes the electronics within the base unit 102 and the lead interface unit 108 to detect and interpret electrical signals from the heart of the patient P. The electrical signals are recorded by the electrocardiograph instrument 100 in a computer readable storage device, and can be output in a variety of manners, including by printing the electrical signals on paper, displaying the electrical signals on a display, or transferring digital data representing the electrical signals to another device, such as across a data communication network. Examples of the base unit 102 and the lead interface unit 108 are illustrated and described in more detail herein.

The instrument 100 also includes electrode contact quality evaluation circuitry 120, which operates to evaluate the quality of the contact between the electrodes and skin of the patient P. In some embodiments the electrode contact quality evaluation circuitry 120 is part of the lead interface unit 108, as shown in FIG. 1, while in other embodiments the circuitry 120 is part of the base unit 102, or a combination of the base unit 102 and the lead interface unit 108. One or more different or additional units may also be included in some embodiments, which may alternatively include some or all of the circuitry 120. An example of the electrode contact quality evaluation circuitry 120 is illustrated and described in more detail with reference to FIGS. 7-15.

A cable 106 transfers electrical signals between the lead interface unit 108 and the base unit 102, in some embodiments. An example of the cable 106 is illustrated and described in more detail with reference to FIG. 5. The cable 106 is an example of a communication interface. In other possible embodiments, the communication interface is a wireless interface used to transfer digital data between the lead interface unit 108 and the base unit 102.

Leads 110 each include one or more insulated conductors that transfer electrical signals between the lead interface unit 108 and individual electrodes 112. Typically the instrument 100 includes at least three leads 110, and more typically includes a larger number of leads, such as 5, 10, or more. An example is described herein that includes 10 leads. The leads 110 are illustrated and described in more detail herein with reference to FIG. 5.

Electrodes 112 are electrically conductive devices that are configured to be placed on and connected to the surface of the skin S of the patient P. A wide variety of electrodes 112 can be used, including reusable and disposable electrodes. Some electrodes 112 include an adhesive layer for fastening to the skin, while other embodiments use other fasteners, such as a suction-cup type of device. The electrical contact and suction seal of some electrodes can be improved by placing an electrically conductive gel, paste, or creme between the electrode 112 and the skin S. Appropriate skin preparation steps can also be used to improve the electrical contact between the electrodes 112 and the skin. These steps can include shaving, cleansing, and lightly abrading.

Electrodes 112 are typically placed in precise locations on the patient P during electrocardiography. The individual electrodes 112 can be referred to by their locations. Examples of common electrode locations include: V1 (fourth intercostal space at right sternal border), V2 (fourth intercostal space at left sternal border), V3 (midway between V2 and V4), V4 (fifth intercostal space at the left midclavicular line), V5 (anterior axillary line at the same horizontal level as V4), V6 (mid-axillary line on the same horizontal level as V4 and V5), LA (left arm—just above the left wrist on inside of arm), LL (left leg—just above the left ankle), RL (right leg—just above the right ankle), RA (right arm—just above the right wrist on inside of arm). Other electrode arrangements are used at other times or with other embodiments. For example, a different arrangement may be used with small children.

Figure 2:
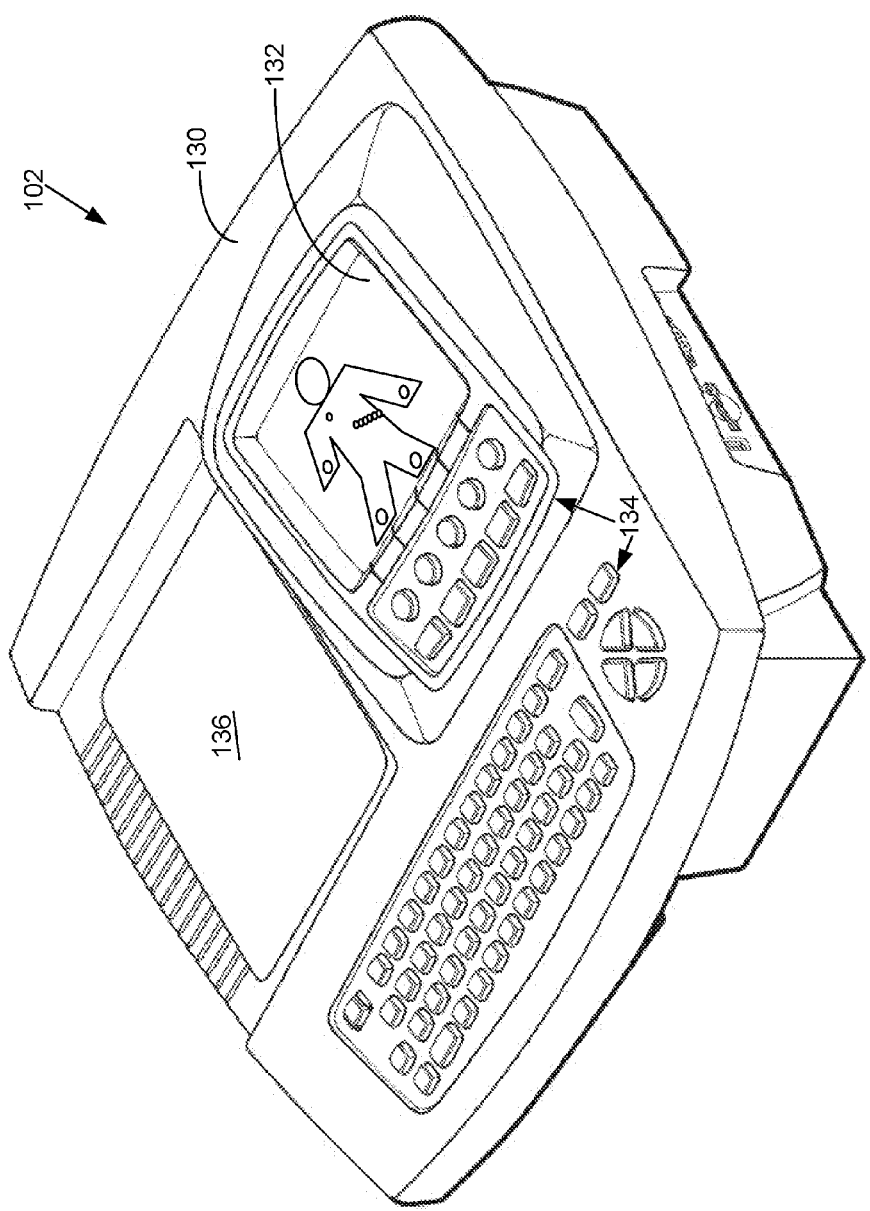
FIG. 2 is a perspective view of an example base unit of the instrument shown in FIG. 1.
Figure 3:
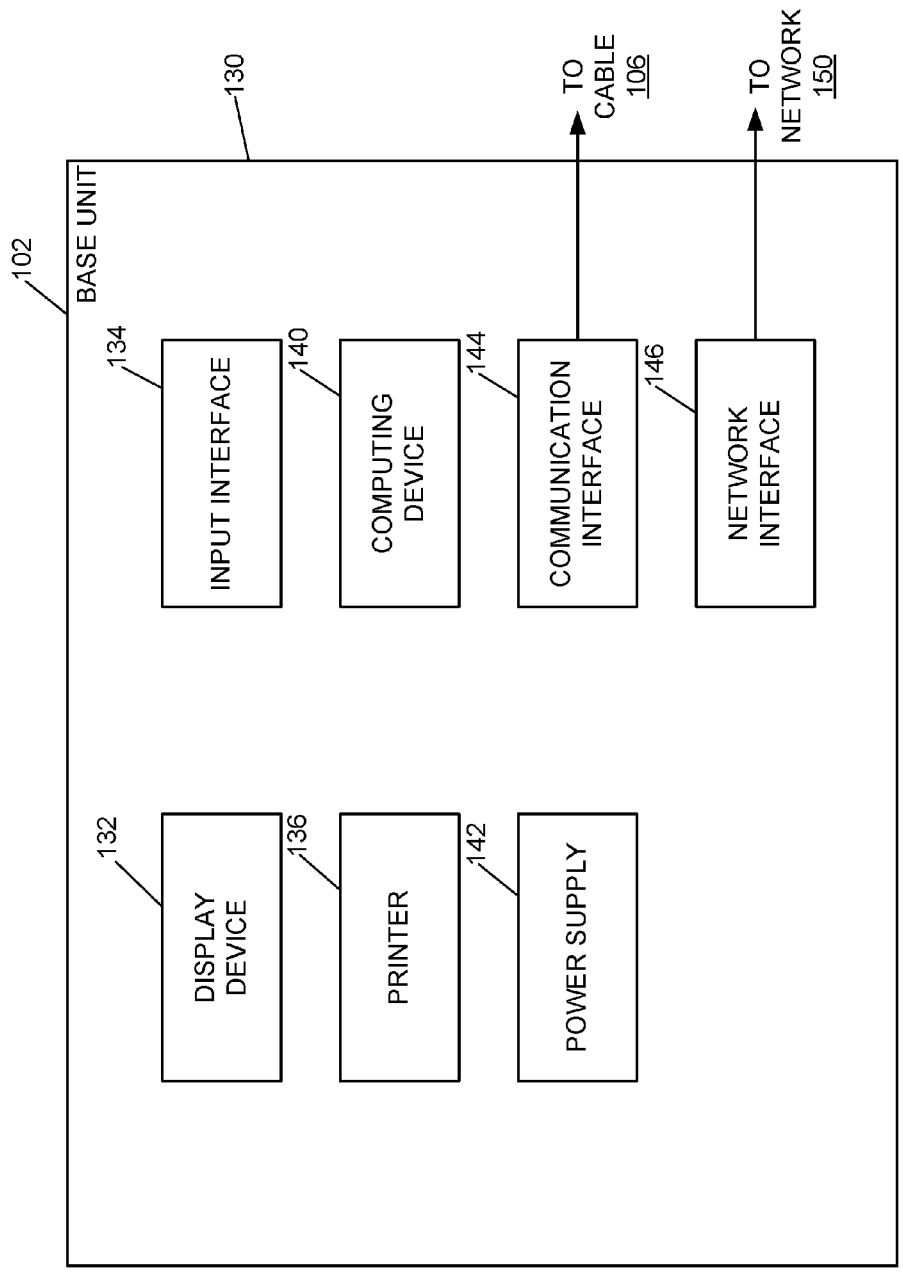
FIG. 3 is a schematic block diagram of the base unit shown in FIG. 2.

FIGS. 2 and 3 illustrate an example of the base unit 102, shown in FIG. 1. FIG. 2 is a perspective view of the base unit 102 and FIG. 3 is a schematic block diagram of the base unit 102. In this example, the base unit 102 includes a housing 130, a display device 132, an input interface 134, a printer 136, a computing device 140, a power supply 142, a communication interface 144, and a network interface 146.

The housing 130 provides a protective enclosure for base unit electronics contained therein.

The display device 132 is a device that generates a visual user interface to convey information to a user, such as a clinician. Examples of displays 132 include liquid crystal displays, light emitting diode (LED) displays, and the like.

The input interface 134 operates to receive input from a user, such as through a plurality of selectable buttons. The buttons can be arranged in a keyboard configuration, and can include additional controls for selecting options presented on the display device 132. One or more switches can be used to detect user-inputs in some embodiments. The input interface 134 can include a variety of other possible devices in other embodiments, such as a microphone for receiving voice commands, a wireless interface for receiving input through a wireless device, such as a remote control or keypad, a network communication device for receiving inputs from or sending data to a remote device, etc.

The printer 136 prints reports related to the electrocardiogram. In some embodiments the printer 136 prints reports that graphically depict one or more electrical signals that were detected from the patient's heart.

The computing device 140 includes at least a processing device and at least one computer readable storage device. The processing device operates to execute data instructions stored in the computer readable storage device to perform various operations, methods, or functions described herein. An example of the computing device 140 is illustrated and described in more detail with reference to FIG. 4.

The power supply 142 typically receives power from an external source, such as through a power cord that can be connected to a wall receptacle. In some embodiments the power supply includes an alternating current (AC) to direct current (DC) converter, as well as various filtering and surge protection circuitry, and supplies power at a suitable level to electronics contained within the housing 130, as well as to the lead interface unit 108 through cable 106. Other possible embodiments include other power sources, such as a battery power supply.

The communication interface 144 includes circuitry to communicate with the lead interface unit 108, such as through cable 106. In another possible embodiment, the communication interface 144 includes a wireless receiver, or transceiver for communicating wirelessly with the lead interface unit 108.

The network interface 146 includes a network communication device that operates to communicate digital data across a data communication network 150. An example of the network interface 146 is an Ethernet network interface device having an Ethernet port for receiving an Ethernet cable and transmitting and receiving digital data across the Ethernet cable to a network 150 such as a local area network or the Internet. In other possible embodiments, the network interface 146 includes one or more of a wireless communication device such as a cellular communication device, a Wi-Fi communication device (such as conforming to one of the IEEE 802.11 family of communication protocols), a Bluetooth® communication device, and the like. In some embodiments the network interface 146 is a part of the computing device 140, as illustrated in FIG. 4.

Figure 4:
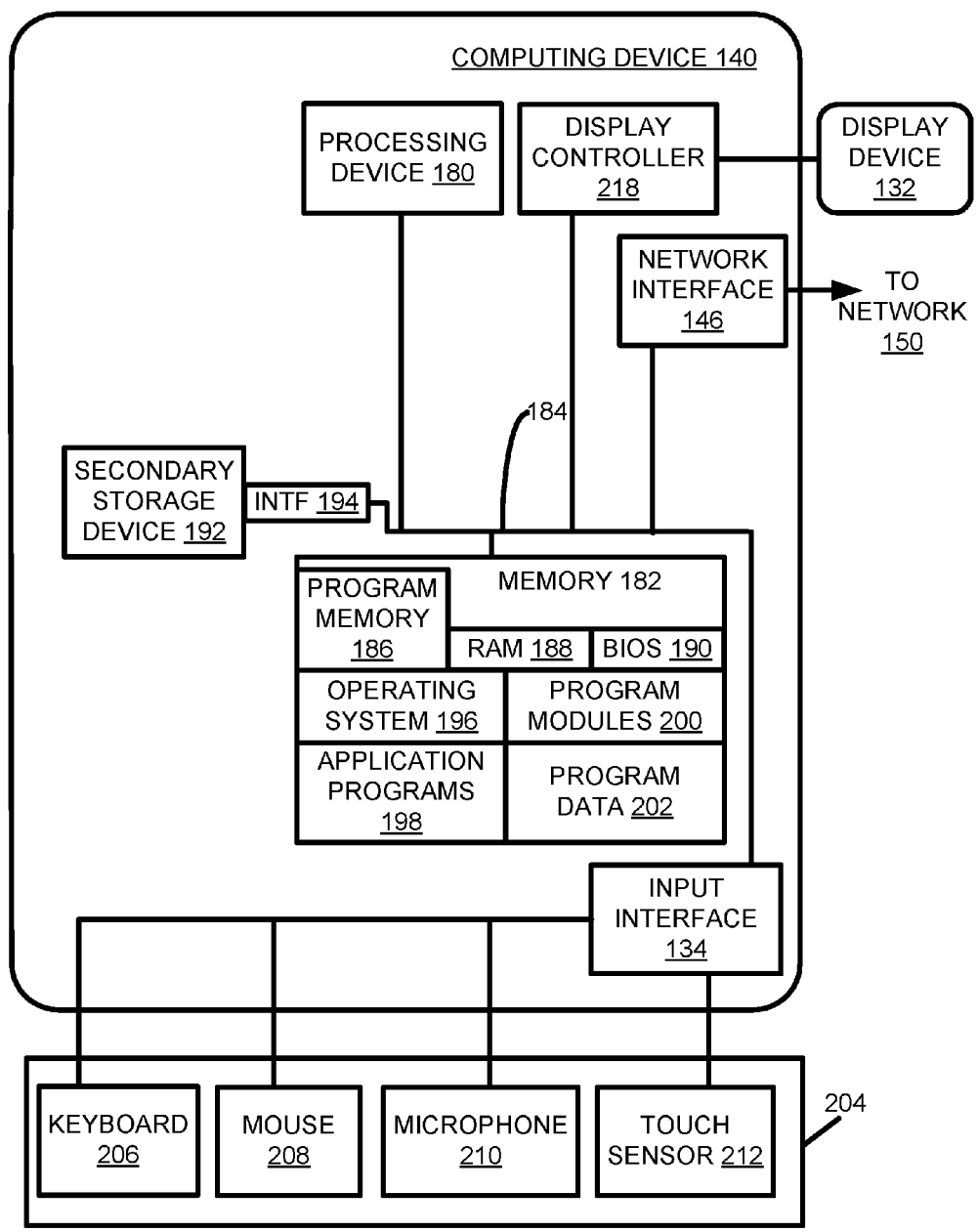
FIG. 4 illustrates an exemplary architecture of a computing device of the base unit shown in FIG. 2.

FIG. 4 illustrates an exemplary architecture of a computing device that can be used to implement aspects of the present disclosure, including the computing device 140 of the base unit 102. The computing device illustrated in FIG. 4 can be used to execute any one or more of the operating system, application programs, software modules, and software engines, as described herein. By way of example, the computing device will be described below as computing device 140 of the base unit, although additional computing devices can be included in some embodiments, such as one or more computing devices that are in data communication with the computing device 140 across data communication network 150. To avoid undue repetition, this description of the computing device will not be separately repeated herein for each of the other possible computing devices, but such devices can also be configured as illustrated and described with reference to FIG. 4.

The computing device 140 includes, in some embodiments, at least one processing device 180, such as a central processing unit (CPU). A variety of processing devices are available from a variety of manufacturers, for example, Intel or Advanced Micro Devices (AMD). In this example, the computing device 140 also includes a system memory 182, and a system bus 184 that couples various system components including the system memory 182 to the processing device 180. The system bus 184 is one of any number of types of bus structures including a memory bus; a peripheral bus; and a local bus using any of a variety of bus architectures.

Examples of computing devices suitable for the computing device 140 include a microcontroller, a microprocessor, a desktop computer, a laptop computer, a tablet computer, a mobile computing device (such as a smart phone, an iPod® or iPad® mobile digital device, or other mobile devices), or other devices configured to process digital instructions, although in typical embodiments the computing device 140 is a part of the base unit 102 (FIGS. 2-3) and does not include a separate housing.

The system memory 182 includes program memory 186 and random access memory 188. A basic input/output system 190 containing the basic routines that act to transfer information within computing device 140, such as during start up, is typically stored in the program memory 186.

The computing device 140 also includes a secondary storage device 192 in some embodiments, such as a hard disk drive, for storing digital data. The secondary storage device 192 is connected to the system bus 184 by a secondary storage interface 194. The secondary storage devices 192 and their associated computer readable media provide non-volatile storage of computer readable instructions (including application programs and program modules), data structures, and other data for the computing device 140.

Although the exemplary environment described herein employs a hard disk drive as a secondary storage device, other types of computer readable storage media are used in other embodiments. Examples of these other types of computer readable storage media include magnetic cassettes, flash memory cards, digital video disks, Bernoulli cartridges, compact disc memories, digital versatile disk memories, random access memories. Some embodiments include non-transitory media. Additionally, such computer readable storage media can include local storage or cloud-based storage.

A number of program modules can be stored in secondary storage device 192 or memory 182, including an operating system 196, one or more application programs 198, other program modules 200 (such as the software engines described herein), and program data 202. The computing device 140 can utilize any suitable operating system, such as Microsoft Windows™, Google Chrome™, Apple OS, and any other operating system suitable for a computing device. Other examples can include Microsoft, Google, or Apple operating systems, or any other suitable operating system used in tablet computing devices.

In some embodiments, a user provides inputs to the computing device 140 through one or more input devices 204. Examples of input devices 204 include a keyboard 206, mouse 208, microphone 210, and touch sensor 212 (such as a touchpad or touch sensitive display). Other embodiments include other input devices 204. The input devices are often connected to the processing device 180 through an input interface 134 that is coupled to the system bus 184. These input devices 204 can be connected by any number of input/output interfaces, such as a parallel port, serial port, game port, universal serial bus, or a custom interface. Wireless communication between input devices and the interface 134 is possible as well, and includes infrared, BLUETOOTH® wireless technology, 802.11a/b/g/n, cellular, or other radio frequency communication systems in some possible embodiments.

In this example embodiment, a display device 132, such as a monitor, liquid crystal display device, projector, or touch sensitive display device, is also connected to the system bus 184 via an interface, such as a display controller 218. In addition to the display device 132, the computing device 140 can control various other peripheral devices (not shown), such as a speaker or a printer.

When used in a local area networking environment or a wide area networking environment (such as the Internet), the computing device 140 is typically connected to the network 150 through a network interface 146, such as an Ethernet interface. Other possible embodiments use other communication devices. For example, some embodiments of the computing device 140 include a modem for communicating across the network 150. Wireless communication with the network 150 is also possible through a wireless communication device, such as described herein.

The computing device 140 typically includes at least some form of computer readable media. Computer readable media includes any available media that can be accessed by the computing device 140. By way of example, computer readable media include computer readable storage media and computer readable communication media.

Computer readable storage media includes volatile and nonvolatile, removable and non-removable media implemented in any device configured to store information such as computer readable instructions, data structures, program modules or other data. Computer readable storage media includes, but is not limited to, random access memory, read only memory, electrically erasable programmable read only memory, flash memory or other memory technology, compact disc read only memory, digital versatile disks or other optical storage, magnetic cassettes, magnetic tape, magnetic disk storage or other magnetic storage devices, or any other medium that can be used to store the desired information and that can be accessed by the computing device 140.

Computer readable communication media typically embodies computer readable instructions, data structures, program modules or other data in a modulated data signal such as a carrier wave or other transport mechanism and includes any information delivery media. The term "modulated data signal" refers to a signal that has one or more of its characteristics set or changed in such a manner as to encode information in the signal. By way of example, computer readable communication media includes wired media such as a wired network or direct-wired connection, and wireless media such as acoustic, radio frequency, infrared, and other wireless media. Combinations of any of the above are also included within the scope of computer readable media.

The computing device illustrated in FIG. 4 is also an example of programmable electronics, which may include one or more such computing devices, and when multiple computing devices are included, such computing devices can be coupled together with a suitable data communication network so as to collectively perform the various functions, methods, or operations disclosed herein.

Figure 5:
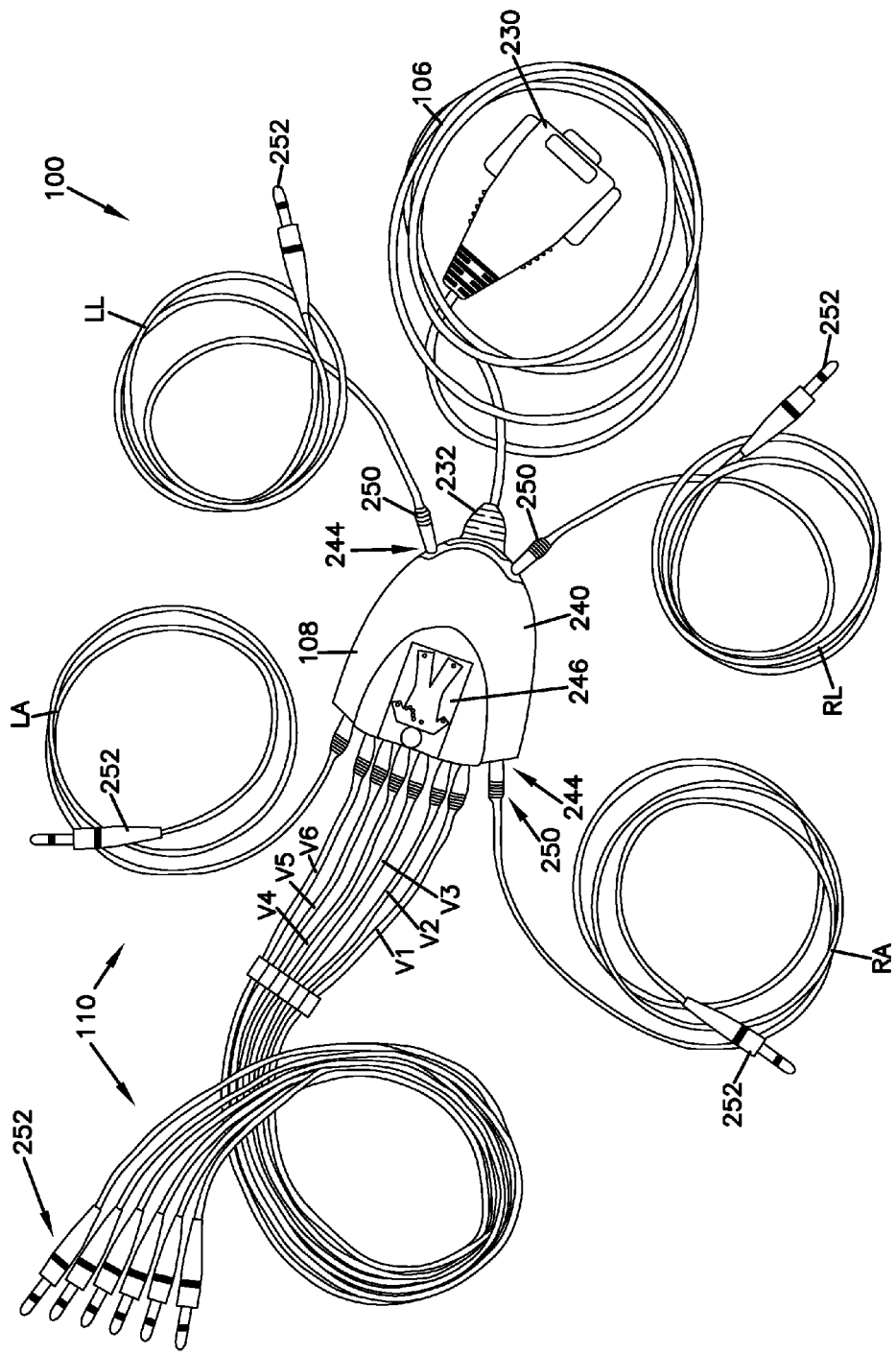
FIG. 5 illustrates several components of the example instrument shown in FIG. 1, including a cable, a lead interface unit, and leads.

FIG. 5 illustrates various components of the example instrument 100 (shown in FIG. 1), including the cable 106, the lead interface unit 108, and the leads 110.

The cable 106 includes electrical conductors enclosed in one or more electrically insulating layers. In this example, the cable 106 includes a plug end 230 configured to be connected to a mating port on the base unit 102 (shown in FIG. 2). The other end 232 of the cable 106 is permanently connected to the housing of the lead interface unit 108, in this example. During operation, the cable 106 is connected to the mating port on the base unit 102, and the cable conducts electrical signals between the lead interface unit 108 and the base unit 102.

In some embodiments the lead interface unit 108 includes a housing 240, electronic components 242 contained within the housing (and not visible in FIG. 5), a plurality of lead interface ports 244, and an electrode connection display device 246. The lead interface unit 108 is typically sized to fit within the hand of a person, and configured so that it can be placed near to the patient during an ECG procedure. Although the electronic components 242 can alternatively be contained within the base unit 102, placement of the electronic components 242 within the lead interface unit 108 reduces the necessary length of the leads 110, and improves the quality of the signals obtained by reducing the electromagnetic interference received by the leads.

An example of the lead interface unit 108 is illustrated and described in more detail herein with reference to FIGS. 7-15.

In some embodiments the lead interface unit 108 includes an electrode connection display device 246. The electrode connection display device 246 provides feedback to the user regarding the electrode connection status. In some embodiments, the electrode connection display device 246 indicates whether the electrodes 112 (connected to leads 110, and shown in FIGS. 1 and 6) have been connected to the patient P (shown in FIG. 1). In other embodiments, the electrode connection display device 246 indicates the quality of the connection between the electrode 112 and the patient P.

In some embodiments the electrode connection display device 246 includes lights, such as light emitting diodes (LEDs) that are selectively illuminated by the lead interface unit 108 to convey information to the user. In another possible embodiment, the electrode connection display device 246 is a display device, such as an LCD display.

In one example embodiment, the electrode connection display device 246 indicates whether the electrodes 112 are connected to the patient. For example, an LED emitting a first color (e.g., green) may indicate that one of the electrodes 112 is connected, while an LED emitting a second color (e.g., white), or off, may indicate that the electrode 112 is not connected.

In another possible embodiment, the electrode connection display device 246 indicates the quality of the connection between the electrode 112 and the patient P. In this example, a first color (e.g., green) may indicate a good connection, a second color (e.g., yellow) may indicate a poor connection, and a third color (e.g., red, blue, or off) may indicate that no connection is detected.

The leads 110 include one or more electrical conductors that are enclosed in one or more electrically insulating materials. In this example, the leads 110 include a lead interface plug end 250 and an electrode plug end 252. The plug end 250 includes a plug that is configured to be inserted within the lead interface ports 244, to physically connect the leads 110 to the lead interface unit 108, and to electrically connect the lead 110 conductors to the electronic components 242 of the lead interface unit 108. The plug end 252 includes a plug that is configured to be inserted into a clip 260 (such as shown in FIG. 6), to physically connect the lead 110 to the clip 260, and to electrically connect a conductor in the lead 110 to a conductor in the clip 260.

Other embodiments include other types of leads 110, which can have different ends. For example, plug end 252 can alternatively include a pinch clip end, a snap end, or other terminating device. In addition, either of the plug end 250 or the plug end 252 can be permanently connected to the lead interface unit 108 or the electrodes 112 respectively. Other terminating devices can be used in other embodiments.

The electrodes 112 are placed at precise locations on the body, and the electrodes 112 and corresponding leads 110 can be referred to by these locations. In this example, the locations include: V1 (fourth intercostal space at the right sternal border), V2 (fourth intercostal space at the left sternal border), V3 (midway between V2 and V4), V4 (fifth intercostal space at the left midclavicular line), V5 (anterior axillary line at the same horizontal level as V4), V6 (midaxillary line on the same horizontal level as V4 and V5), LA (left arm—just above the left wrist on inside of arm), LL (left leg—just above the left ankle), RL (right leg—just above the right ankle), RA (right arm—just above the right wrist on inside of arm). Other electrode configurations can be used, however, in which case the leads can be referred to by the alternate positions. For example, an alternate configuration can be used on a small child where the standard positions may be too closely positioned.

Figure 6:
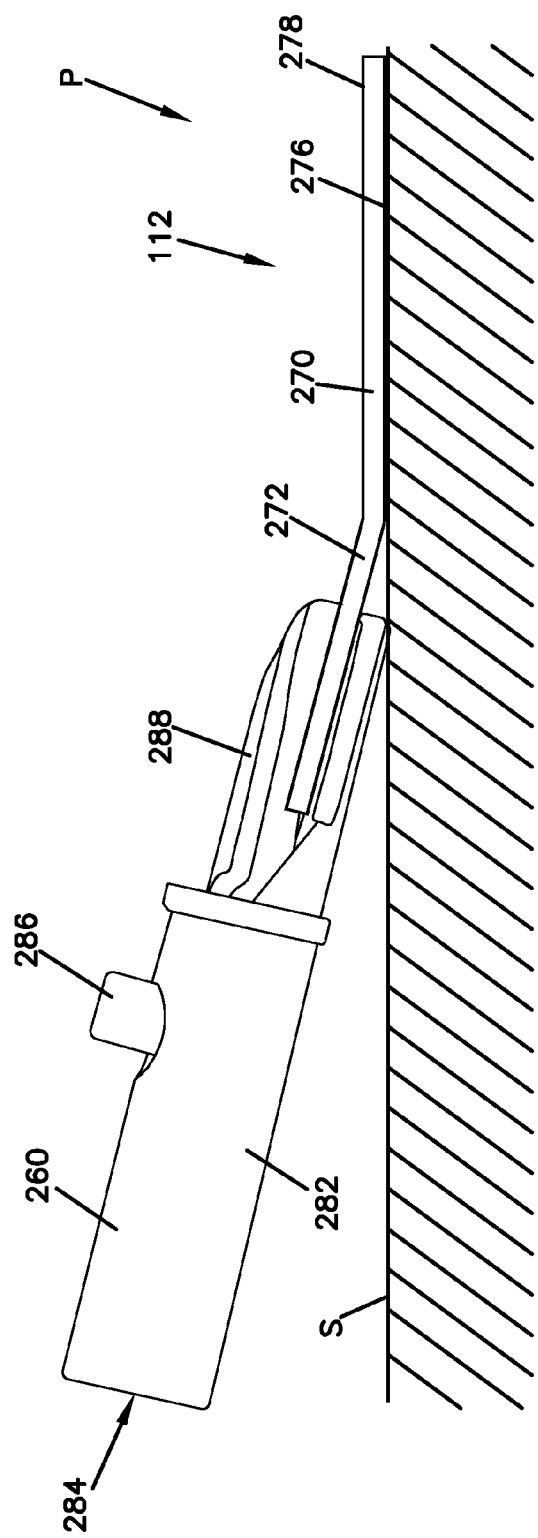
FIG. 6 is a side view illustrating an example clip and an example electrode applied to the skin of a patient.

FIG. 6 is a side view illustrating an example clip 260 and an example electrode 112 applied to the skin S of a patient P.

As discussed herein, a variety of different types of electrodes 112 with various embodiments of instrument 100, and some instruments 100 themselves can be used with various different types of electrodes 112. FIG. 6 illustrates one example including a disposable electrode 112. The disposable electrode includes a body 270 and a tab 272. The body 270 is formed of an insulating substrate material, such as foam or other flexible resilient material. A conductive material is provided on a skin-facing surface 276 of the body 270 to make an electrical connection with the skin S of the patient P. The conductive material is electrically connected to the tab 272, which also includes a conductive material on at least one surface of the tab 272.

The clip 260 can be fastened to the tab 272 to make an electrical connection with the conductive material on the tab 272. In this example, the clip 260 includes a body 282, lead connection port 284, jaw actuation button 286, and jaws 288.

A lead connection port 284 is formed at one end of the body 282 to receive a plug end 252 of one of the leads 110 (shown in FIG. 5). When the plug end 252 is inserted into the lead connection port 284, the body 282 makes a physical connection with the lead 110. In addition, an electrical conductor within the body is positioned to connect with the plug end 252 to make an electrical connection with a conductor in the lead 110.

The electrical conductor of the clip 260 extends out from the body and into the jaws 288. The jaws 288 are spring loaded in a closed position, but can be opened by depressing the jaw actuation button 286.

To connect the clip 260 to the electrode 112, the button 286 is depressed to open the jaws 288. The jaws 288 are then arranged on either side of the tab 272 and the button 286 is released to cause the jaws 288 to clamp onto the tab 272. The electrical conductor on the tab 272 is then electrically connected to the electrical conductor within the jaws 288. When all connections have been made as described with reference to FIGS. 5 and 6, the electrode 112 is electrically connected with the lead interface unit 108, shown in FIG. 5.

The electrode 112 can be fastened to the skin S of the patient P in a variety of manners. In some embodiments, the skin-facing surface 276 of the electrode includes an adhesive layer or coating that fastens the electrode 112 to the skin S. Some embodiments utilize one or more straps, bands, wraps, or other fasteners to apply a force to an opposite surface 278 of the electrode 112 to press the skin-facing surface 276 against the skin S of the patient. Other fasteners or combinations of fasteners can be used in other embodiments.

The quality of the electrical connection between the skin S and the skin-facing surface 276 of the electrode 112 can be greatly improved if proper skin preparation steps are performed prior to placement of the electrodes on the skin S. These steps typically include: shaving or clipping hair from the surface of the skin S, lightly abrading the skin with a gauze pad or other lightly abrasive material to remove dead or loose skin, and cleansing the skin with alcohol or soap and water to remove skin oils.

In addition, electrodes 112 should be properly used and prepared. For example, disposable electrodes are typically provided in sealed packages, and should be kept in the sealed packages until they are ready to be used. Disposable electrodes are often packaged with a conductive gel arranged on the skin-facing surface 276. This gel contains a desired amount of moisture, and can become dried out if prematurely removed from the packaging. If removed from the packaging, the electrodes should be kept in a sealed bag to prevent or reduce evaporation. The disposable electrodes should also be stored away from heat sources to prevent drying or other damage to the electrodes. If reusable electrodes are used, they should be cleaned and used according to manufacturer recommendations.

If a user fails to take the appropriate skin-preparation steps, or fails to follow manufacturer's electrode storage, application, or usage guidelines, the quality of the electrical connection between the electrode 112 and the skin S can be reduced. A poor quality connection results in an increased electrical contact impedance between the electrode 112 and the patient's internal tissues beneath the skin S.

When the quality of the electrical connection between the electrode 112 and the skin is reduced, the quality of signals obtained by the instrument 100 (FIG. 1) can also be reduced, or the instrument 100 can even be rendered entirely inoperable for the intended purpose. For example, the increased impedance can increase the interference caused by power line frequencies or radio frequency noise present in the environment. The increased impedance can also increase artifacts in detected signals caused by physical movement of the electrodes 112 or leads 110. If the quality of the electrical connection is very low, the electrical impedance can increase to such a level that the instrument 100 is unable to obtain adequate electrical signals through the electrodes 112, rendering the instrument inoperable for some or all of its intended purpose(s).

Accordingly, as described herein, the instrument 100 includes electrode contact quality evaluation circuitry 120 (shown in FIG. 1 and illustrated and described in more detail herein) that evaluates the quality of the electrical connection between each electrode 112 and the skin S. Feedback can then be provided to the user to identify the quality of each electrical connection so that the user can fix poor connections, or the quality data can be stored or transmitted for subsequent use. In some embodiments, the instrument 100 requires a certain level of electrode contact quality be detected before the instrument 100 will proceed with subsequent operations.

Figure 7:
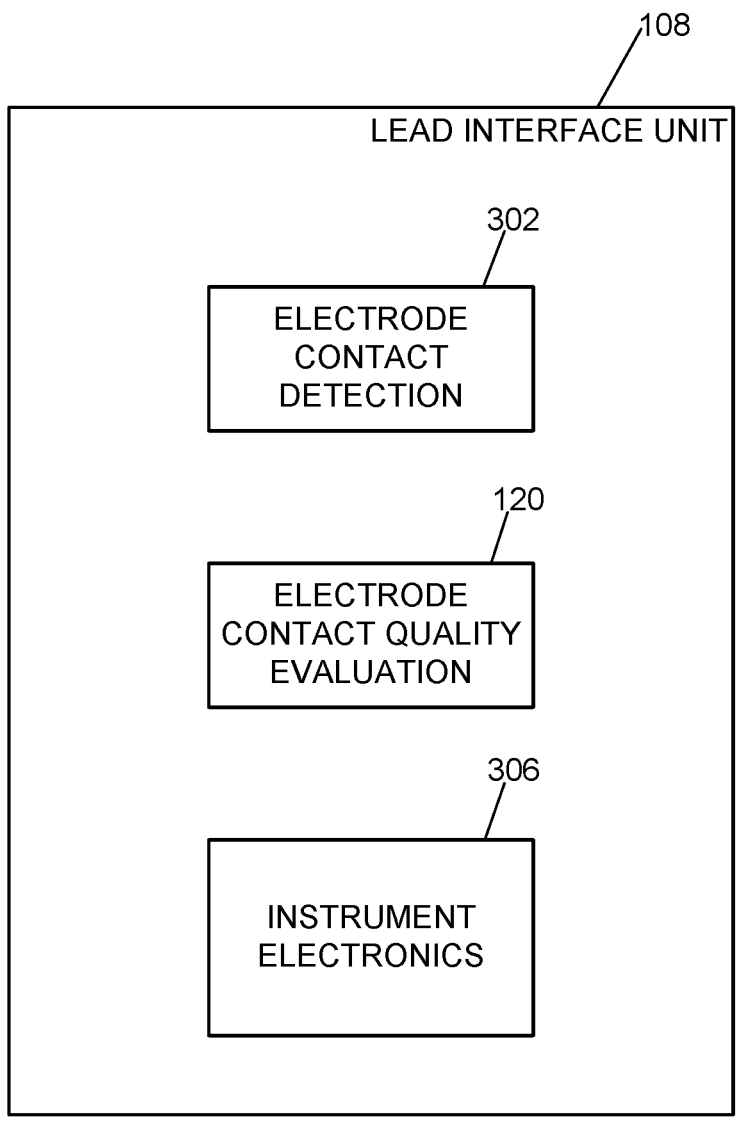
FIG. 7 is a functional block diagram of an example of the lead interface unit shown in FIG. 5.

FIG. 7 is a functional block diagram of an example lead interface unit 108 according to the present disclosure. In this example, the lead interface unit 108 includes electrode contact detection circuitry 302, electrode contact quality evaluation circuitry 120, and instrument electronics 306. A schematic block diagram illustrating an example hardware configuration corresponding to the lead interface unit 108 shown in FIG. 7 is illustrated and described in more detail herein with reference to FIG. 8.

The electrode contact detection circuitry 302 operates to determine whether the electrodes 112 have been placed on the skin S of the patient P, and whether all appropriate connections have been made between the electrodes 112 and the lead interface unit 108. In other words, in some embodiments the electrode contact detection circuitry 302 operates to determine whether an electrical connection has been made through the lead interface unit 108 and the respective electrodes 112 to the patient, regardless of the quality of the connection. For example, the electrode contact detection circuitry 302 can indicate whether each individual electrode 112 is "connected" or "not connected." In some embodiments, the electrode contact detection circuitry 302 applies tiny "lead fail detection" currents to each lead 110, and measures the DC voltage component of the signal on each lead 110 with respect to the common (i.e. "ground") of the floating power supply of the lead interface unit 108. When a lead or its electrode is not connected, that lead's dc voltage component will be far from "ground." This is interpreted as "not connected." The electrode which is used as a reference or return provides a path to sink the lead fail detection currents through the patient's body. If the reference lead and its electrode are connected to the patient's body, then any other electrode and lead connection to the patient will be pulled closer to ground, and that condition is interpreted as "connected." This method requires at least the reference electrode and one other electrode connection before any connection can be detected, i.e., the connection of no single electrode can be detected in this way. To facilitate detection, the choice of reference electrode may optionally be cycled amongst each of the electrode possibilities until one other electrode connection is thus detected or a fixed choice of reference electrode may be used. All subsequent additional electrode connections may be detected using this same choice of reference electrode. The reference electrode itself will always show as connected. If an alternative choice of reference electrode has been selected while searching for electrode contact, the preferred choice of reference electrode may be selected after sufficient electrodes are determined to be in contact with the patient. In some embodiments, the electrode contact detection circuitry 302 is included within the instrument electronics 306.

The electrode contact quality evaluation circuitry 120 operates to determine the quality of the connection between individual electrodes 112 and the skin S of the patient P. The quality is measured as an electrical impedance, where a higher impedance indicates a lower quality connection and a lower impedance indicates a higher quality connection. In some embodiments the electrode contact quality is further simplified by assigning the electrical impedance one of a plurality of possible quality levels. For example, the quality may be selected from one of a plurality of quality levels, such as "unsatisfactory," and "satisfactory." In another embodiment, the quality levels include, "poor," "marginal," and "good." Additional or different quality levels including a simple ranking number are used in other embodiments.

In some embodiments, the electrode contact quality evaluation circuitry can inhibit instrument 100 from proceeding with instrument operations (utilizing instrument electronics 306) until the electrode contact quality has been determined to meet or exceed a predetermined quality level, such as at least "satisfactory" or at least "marginal," in the examples listed above.

The instrument electronics 306 perform the main instrument operations. For example, when the instrument is an ECG instrument, the instrument electronics 306 include ECG acquisition electronics to receive electrical signals from the heart. The ECG electronics can also perform other operations, as desired for the instrument. Other instruments perform other operations. For example, an EEG instrument includes EEG acquisition electronics that operate to obtain electrical activity along the scalp of a patient. An EMG instrument includes EMG acquisition electronics that operate to obtain electrical activity produced by skeletal muscles. Other instruments include other instrument electronics 306.

As discussed elsewhere herein, although the example shown in FIG. 7 illustrates and describes the components 302, 120, and 306 with reference to an example embodiment in which the components 302, 120, and 306 are part of the lead interface unit 108, in other possible embodiments one or more of the components 302, 120, and 306 are included as part of the base unit 102, or another portion of the instrument 100 (shown in FIG. 1), as desired. Some embodiments include a shared trunk cable between the lead interface unit and the individual leads. Further, some embodiments do not include each of the components 302, 120, and 306.

The lead interface unit 108 typically also includes a lead interface, best seen in FIG. 5. In some embodiments, the lead interface includes a plurality of ports 244 (which may include jacks or other receptacles, for example) that are configured to receive plug ends 250 of the leads 110 to make physical and electrical connections between the lead interface unit 108 and the leads 110. In other embodiments, the lead interface includes a terminal block for connecting the leads 110 to the lead interface unit 108. The leads 110 can also be permanently connected to the lead interface unit 108 in yet other embodiments.

Figure 8:
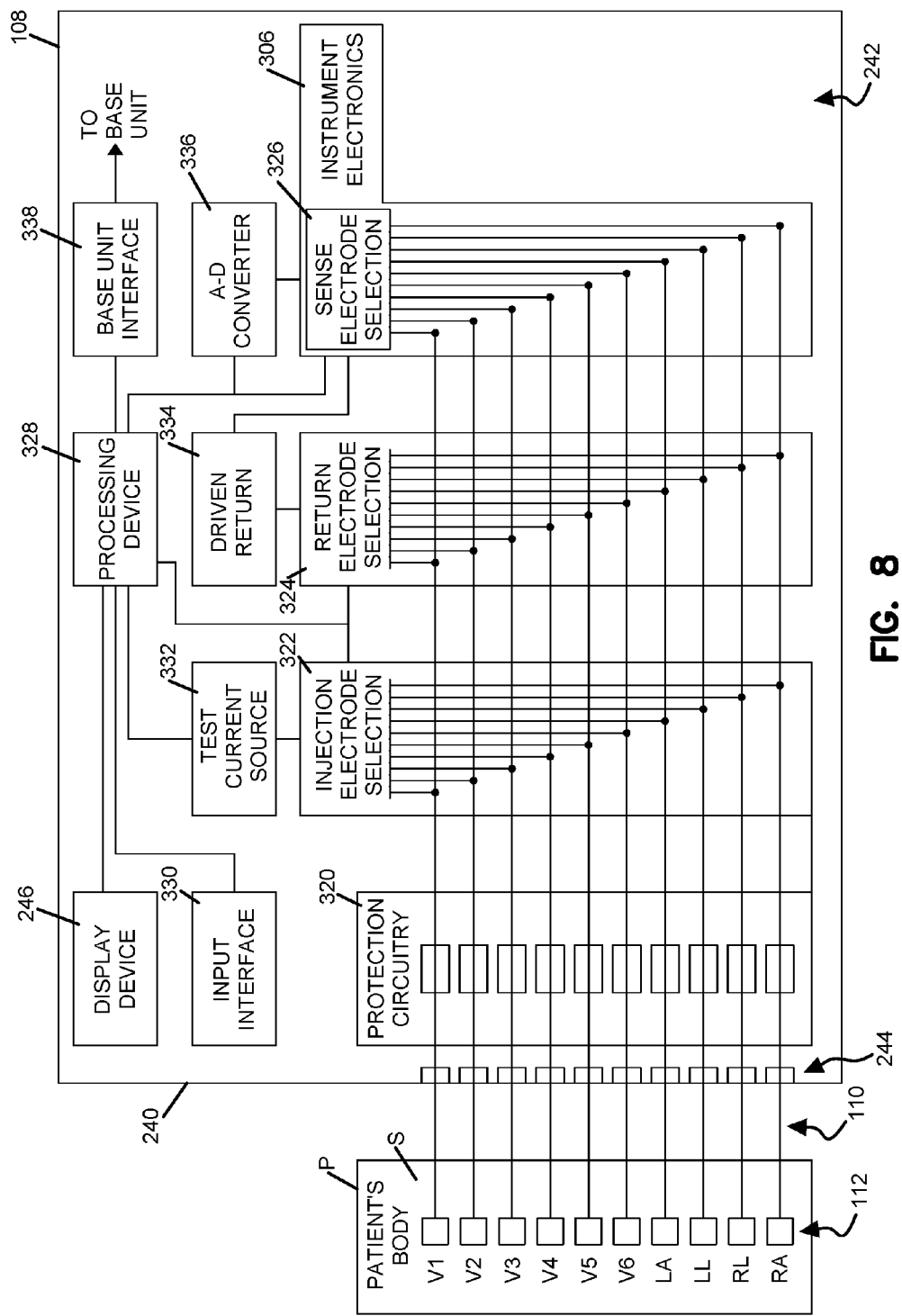
FIG. 8 is a schematic block diagram illustrating an example hardware configuration of the lead interface unit shown in FIG. 5.

FIG. 8 is a schematic block diagram illustrating an example hardware configuration corresponding to the lead interface unit 108, shown in FIG. 7, and also illustrating leads 110, and electrodes 112.

In this example, the lead interface unit 108 includes a housing 240, electronic components 242 contained within the housing, a plurality of lead interface ports 244, and an electrode connection display device 246, as shown in FIG. 5. In some embodiments, the electronic components 242 include instrument electronics 306, protection circuitry 320, injection electrode selection circuitry 322, return electrode selection circuitry 324, sense electrode selection circuitry 326, a processing device 328, an input interface 330, a test current source 332, driven return circuitry 334, an analog to digital converter 336, and a base unit interface 338.

The electrodes 112 are arranged at specific locations on the skin S of the patient P, and are connected to the appropriate leads 110 to form an electrical connection between the skin S and the lead interface unit 108. In this example, ten electrodes are used, which are placed at the following locations (which are each described in more detail herein) on the skin S of the patient P: V1, V2 V3, V4, V5, V6, LA, LL, RL, RA. Other electrode and lead configurations and quantities are used in other embodiments.

The leads 110 connect between the electrodes 112 and the respective lead interface ports 244 on the housing 240 of the lead interface unit 108.

Protection circuitry 320 is provided in some embodiments, which protects the electronic components 242 from external electric currents, such as from a defibrillator. The protection circuitry 320 can include a resistor, for example, to limit current flow from the leads 110. In some embodiments the protection circuitry 320 includes a clamp circuit that limits the magnitude of the input signal. The clamp circuit can include, for example, a zener diode, a neon bulb, or a gas discharge tube. Some embodiments also include one or more stages of passive low pass filter between the clamp circuits and the rest of the circuits. These low pass filters not only reduce susceptibility to RF interference and provide additional protection against damage from defibrillator discharges, but the series resistor(s) in them also serve to limit the maximum current that can be applied through the patient during single fault conditions of the circuitry 242.

In some embodiments the electrode contact quality evaluation circuitry 120 includes electrode selection circuitry that permits the selection between the various electrodes 112 to be used for different purposes. In this example, the electrode contact quality evaluation circuitry 120 includes injection electrode selection circuitry 322, return electrode selection circuitry 324, and sense electrode selection circuitry 326. The selection circuitry can be implemented by analog multiplexers, which can be controlled by the processing device to select amongst any one of the leads 110 and corresponding electrodes 112. Once selected, an electrical connection is made between the selected electrode and the appropriate electronic components 242.

The instrument electronics 306 include additional electronics that perform the one or more intended operations of the instrument 100, in addition to the electrode contact detection circuitry 302 and the electrode contact quality evaluation circuitry 120 (shown in FIG. 7). For example, when the instrument 100 is an ECG instrument, the instrument electronics include ECG acquisition electronics. Other embodiments include other instrument electronics. In some embodiments, the instrument electronics 306 may include one or more electrical components that can be utilized by both of the instrument electronics 306 and one or more of the electrode contact detection circuitry 302 and the electrode contact quality evaluation circuitry 120. For example, the sense electrode selection circuitry 326 is part of the instrument electronics 306, and also part of the electrode contact quality evaluation circuitry 120. However, the circuitry can be separated in other possible embodiments, if desired.

The processing device 328 performs control operations for the lead interface unit 108. Examples of processing devices are described herein. In some embodiments, all or a portion of the electrode contact detection circuitry 302, electrode contact quality evaluation circuitry 120, the instrument electronics 306 the return electrode selection circuitry 324, the driven return circuitry 334, the analog to digital converter 336, and sense electrode selection circuitry 326 may be contained in or implemented by one or more application specific integrated circuits ("ASICs") such as Welch Allyn's P/N 442-0016-01 or Texas Instruments' ADS1298 series parts.

The input interface 330 is provided in some embodiments to receive inputs from a user. For example, in an embodiment in which the lead interface unit 108 wirelessly communicates with the base unit 102, the input interface 330 can include a "connect" button to initiate the wireless communication. Other input devices can be provided in some embodiments, such as one or more buttons, switches, touch sensitive displays, and other devices suitable for receiving an input from a user. Some embodiments do not include an input interface 330, and instead the input interface is provided on the base unit 102.

The test current source 332, driven return circuitry 334, and analog to digital converter 336 are parts of the electrode contact quality evaluation circuitry 120, described in more detail herein. (In some embodiments the driven return circuitry 334 and analog to digital converter are shared within the instrument electronics 306.) The test current source 332 generates a test signal that is delivered to one of the leads 110 and electrodes 112 that are selected with the injection electrode selection circuitry 322. The driven return circuitry 334 generates a signal of approximately equal magnitude but of opposite polarity, which is delivered to another one of the leads 110 and electrodes 112 that are selected with the return electrode selection circuitry 324. The resulting signals are then sensed relative to a third one of the leads 110 and electrodes 112 or relative to a selected average of two or three of these that are selected by the sense electrode selection circuitry 326. The resulting signals are converted from an analog into a digital form by the analog to digital converter 336, and processed by the processing device 328.

In most embodiments the test signal generated by the test current source 332 is an alternating current (AC) signal. The AC test signal can be detected independent from the magnitudes of any DC offsets that may be present, such that the DC offsets do not impact the readings. In some embodiments, the test current source 332 generates a test signal having a square wave shape. Other embodiments can use other wave shapes, such as sinusoidal or triangular wave shapes, but a square wave is simplest to create.

The AC frequency of the test signal is selected according to several criteria. One criterion is that the frequency should be within the passband of the electronic components 242 and/or instrument electronics 306. Another criterion is that the frequency must be less than half the sampling frequency of the analog to digital converter 336. In an example embodiment, the sampling frequency of the analog to digital conversion is about 1,000 Hz, although other embodiments may have other sampling frequencies. In some embodiments, it is desirable that the test frequency be an even sub-multiple of the sampling frequency, such as (¼) or (⅛) of the sampling frequency. Within these guidelines, a higher frequency will improve the rejection of artifacts. For example, interference generated by a 60 Hz power line will impact the detected signal less if the test frequency is much greater than the 60 Hz frequency. Considering these criteria, some embodiments generate a test signal having a frequency of 125 Hz or 250 Hz.

The analog to digital converter 336 measures signals that are received on the injected and driven return electrodes 112 and corresponding leads 110 relative to the electrode that is selected by the sense electrode selection circuitry 326. In some embodiments one or the average of two or more electrodes 112 and corresponding leads 110 can be selected at one time by the sense electrode selection circuitry 326, provided that none of the AC test current is flowing through the selected sensed electrodes 112 and leads 110, because such current flow would impact the accuracy of the results. Instead, it is desired that no current is flowing through any of the one or more electrodes 112 and leads 110 that are selected by the sense electrode selection circuitry 326.

The signals measured by the analog to digital converter 336 are passed to the processing device 328 for further evaluation. The processing device 328 computes the contact impedances of individual electrodes using the signals detected by the analog to digital converter 336. The contact impedances can then be evaluated to determine the quality of the contact between the individual electrode 112 and the patient P. In some embodiments, the contact impedances for two electrodes can be determined with a single test operation.

The base unit interface 338 includes electronics that handle communications between the lead interface unit 108 and the base unit 102 (FIG. 1). For example, the base unit interface 338 sends data representing the signals generated by the heart of the patient P to the base unit 102 for further processing. The base unit interface 338 can also receive commands from the base unit 102, such as to adjust a mode of operation of the lead interface unit 108 based on inputs received from the user. In some embodiments that include cable 106, the base unit interface 338 also provides electrical isolation between the base unit 102 and the lead interface unit 108.

In some embodiments, the base unit interface 338 is physically and electrically connected to the cable 106, which carries the communication signals between the lead interface unit 108 and the base unit 102. In other embodiments, the base unit interface 338 includes a wireless communication device that wirelessly communicates with the communication interface 144 (FIG. 3) of the base unit 102. Wireless communication approaches inherently include electrical isolation.

Figure 9:
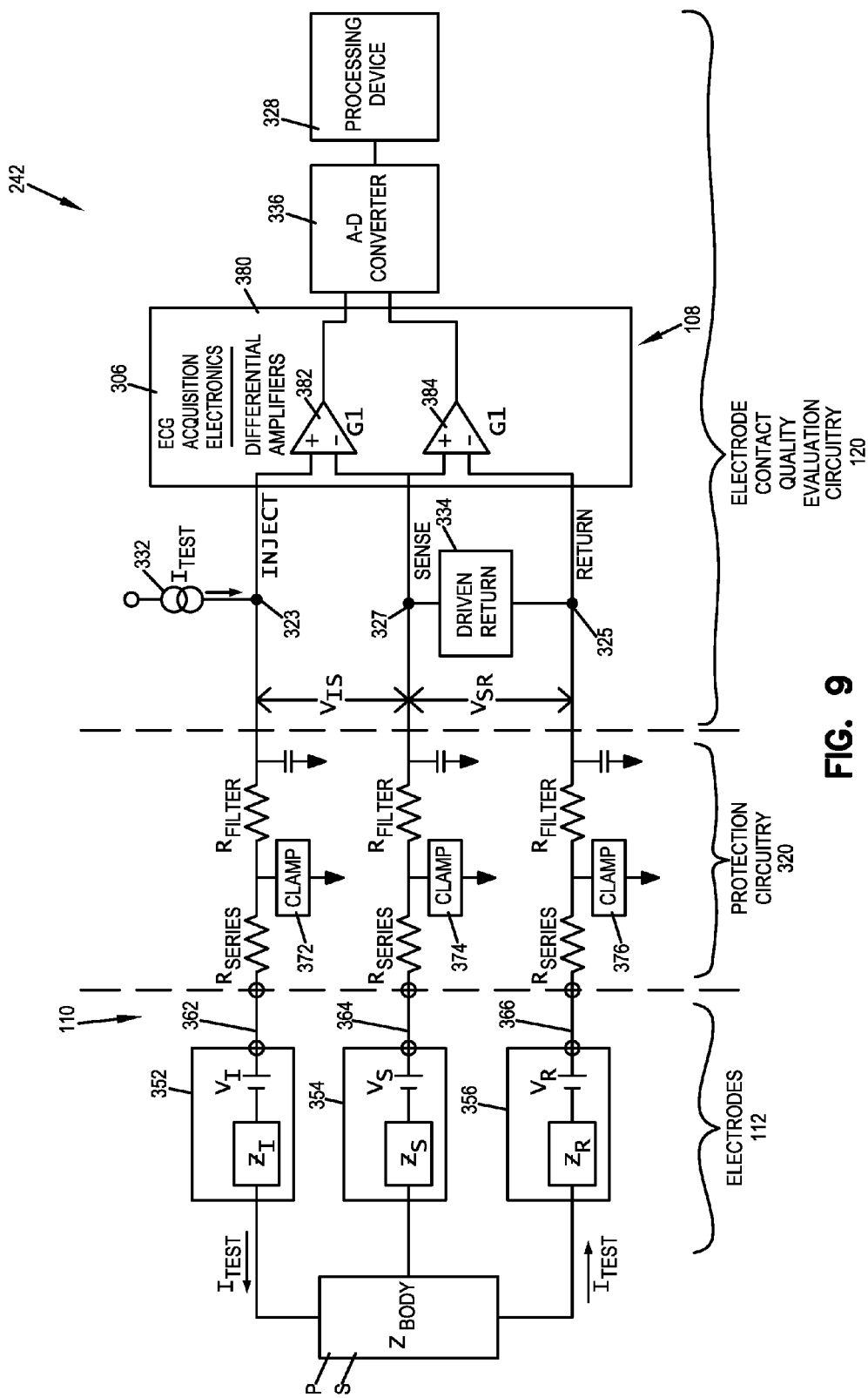
FIG. 9 is a schematic diagram illustrating an example of electrode contact quality evaluation circuitry and its interfaces to the patient.

FIG. 9 is a schematic diagram illustrating an example of the electrode contact quality evaluation circuitry 120, shown in FIG. 7. FIG. 9 also illustrates the connection of the electrode contact quality evaluation circuitry 120 with the skin S of the patient P through the leads 110 and electrodes 112.

In this example, the electronic components 242 of the lead interface unit 108 (shown in FIG. 8) include protection circuitry 320, and electrode contact quality evaluation circuitry 120. In this example, the electrode contact quality evaluation circuitry 120 utilizes at least some of the instrument electronics 306, which in this case include ECG acquisition electronics. The electrode contact quality evaluation circuitry 120 also includes and utilizes the analog to digital converter 336 and the processing device 328. The processing device 328 operates to perform processing operations of the electrode contact quality evaluation circuitry 120 as part of the determination of the quality of electrical connections between the electrodes 112 and the patient P, as described in more detail herein. In addition to the specific function of the processing device 328 illustrated and described in FIG. 9, the processing device 328 also performs control operations in some embodiments to control the operation of the lead interface unit 108 electronic components 242.

The schematic in FIG. 9 is simplified to show only three electrodes 112 (including electrodes 352, 354, and 356) and three associated leads (including leads 362, 364, and 366). The three leads are selected by the selection circuitry 322, 324, and 326 shown in FIG. 8. For example, an injection electrode 352 and lead 362 are selected by the injection electrode selection circuitry 322 (FIG. 8), which makes contact with the selected lead 362 through circuit point 323 (FIG. 9). The sense electrode 354 and lead 364 are selected by the sense electrode selection circuitry 326, which makes contact with the selected lead 364 through circuit point 327.

The return electrode 356 and lead 366 are selected by the return electrode selection circuitry 324, which makes contact with the selected lead 366 through circuit point 325.

The human body is comprised of a large percentage of water, which makes the body a good conductor of electricity. When the electrodes 112 are properly connected to the skin S of the patient's body P, the electrodes 112 make an electrical connection with the body, such that electrical signals can be applied to or detected from the body. Although the body is a good conductor of electricity, it still has some impedance. This impedance is represented by $Z_{BODY}$. Typically the impedance of the body is much lower than other circuit impedances, however, and as a result the impedance of the patient's body $Z_{BODY}$ can typically be ignored and treated as a short circuit amongst the electrodes 112.

When the electrodes 112 are connected to the patient's skin S, a contact impedance exists at the intersection between the electrodes 112 and the patient's skin S. For example, the injection electrode 352 has an impedance $Z_I$, the sense electrode 354 has an impedance $Z_S$, and the return electrode has an impedance $Z_R$. When proper skin preparation steps are performed, and proper electrode application procedures are followed, the electrode contact impedance will be relatively low (e.g., less than 10K ohms). When proper skin preparation steps are not performed, or proper electrode application procedures are not followed, the electrode contact impedance can be an order of magnitude higher, or more (e.g., greater than 120K ohms). The instrument 100 (shown in FIG. 1) operates most effectively when the contact impedances between the electrodes 112 and the skin S are low. High contact impedances can degrade the quality of the detected signals by enabling the pickup and generation of increasing amounts of artifacts along with the desired signals.

In addition to the contact impedances, DC offset voltages can accumulate at the electrodes 112. The DC offsets are represented by voltage sources VI, VS, and VR, for the injection electrode 352, the sense electrode 354, and the return electrode 356, respectively. Due to the possible presence of DC offsets on the electrodes 112, in preferred embodiments the electrode contact quality evaluation circuitry 120 is configured to properly determine electrode contact quality regardless of whether or not such DC offsets are present on the electrodes 112.

The electrodes 112 are each connected to the lead interface unit 108 through one or more leads 110. For example, the injection electrode 352 is connected to injection lead 362, the sense electrode 354 is connected to sense lead 364, and the return electrode 356 is connected to return lead 366. The impedance of the leads 110 is typically negligible and can therefore be ignored in some embodiments and treated as a short circuit.

The protection circuitry 320 is provided to protect the electronic components 242 from large external electrical signals. For example, if a defibrillation shock is delivered to the patient, the protection circuitry operates to protect the electronic components 242 from large currents and voltages that may be applied to the electrodes 112. The protection circuitry 320 can take various forms in different embodiments. In this example, the defibrillation protection circuitry is provided for each lead 110, and comprises a series resistor $R_{SERIES}$ and a clamp circuit 372, 374, and 376, respectively. The resistance of the series resistor is selected according to the needs of the particular implementation, and in view of the external sources that are likely to be encountered. As one example, $R_{SERIES}$ is about 10K ohms. Examples of clamp circuits 372, 374, and 376 are described herein.

In this example, the protection circuitry 320 is provided between the injection current source 332 (circuit point 323) and the lead 362, to protect the injection current source 332. The protection circuitry also includes passive low pass filter circuitry.

In some embodiments, the electrode contact quality evaluation circuitry 120 includes a test current source 332, a driven return 334, differential amplifiers 380 (such as provided by the ECG acquisition electronics 306), an analog to digital converter 336, and a processing device 328. The following discussion describes an exemplary operation of the electrode contact quality evaluation circuitry 120 when the instrument 100 is operating in an electrode contact quality evaluation mode to perform an electrode contact quality evaluation operation. In this example, the contact quality evaluation operation determines the quality of the electrical connections of the injection electrode 352 and the return electrode 356 in a single operation, by determining the corresponding contact impedances.

The test current source 332 generates an AC test signal that is injected into the injection lead 362 and injection electrode 352 at circuit point 323. As discussed herein, the test current source 332 is typically a current source that generates an AC signal at a selected frequency, such as at 125 Hz or 250 Hz, although other frequencies can be used in other embodiments. The current ($I_{TEST}$) flows through the protection circuitry 320, including the series resistors $R_{SERIES}$ and $R_{FILTER}$, through the injection lead 362, and into the electrode 352.

The electronic components 242 operate to select one or more of the electrodes 112 as sense electrode 354 and the corresponding one or more leads 110 as sense lead 364. For example, an average of two or more electrodes 112 can be treated as the sense electrode 354. The electronic components 242 operate so that no significant portion of the test current ($I_{TEST}$) is conducted through the sense electrode 354 and lead 364. In this way, no significant current is conducted through the contact impedance $Z_S$, or the series resistors $R_{SERIES}$ and $R_{FILTER}$, so that no significant voltage related to $I_{TEST}$ is developed across any of these latter impedances. In some embodiments, when multiple electrodes 112 are selected as the sense electrode 354, the signal at circuit point 327 can be an average of the signals at each of the electrodes, which is then provided to the driven return 334.

A driven return 334 is provided in some embodiments to accept the return of the test current ($I_{TEST}$) through the return electrode 356 and the return lead 366. The driven return 334 is electrically coupled between the sense electrode 354 (at circuit point 327) and the return electrode 356 (at circuit point 325) by the sense electrode selection circuitry 326 and the return electrode selection circuitry 324 (both shown in FIG. 8).

The driven return 334 operates to sink all (or substantially all) of the test current ($I_{TEST}$) from the test current source 332 to the return electrode 356 and return lead 366. The driven return 334 operates to keep the voltage at the sense electrode 354 centered at an isolated ground potential for the instrument 100).

In some embodiments, a driven return circuit may also be included within the ECG acquisition electronics 306, which is used by the instrument 100 during a normal operating mode. If so, the driven return of the ECG acquisition electronics 306 can be used as the driven return 334 for purposes of the electrode contact impedance evaluation, rather than including separate circuits.

During the test operation, when the test current ($I_{TEST}$) is being generated by the test current source 332, differential voltages are generated. For example, a voltage differential of $V_{IS}$ is generated between the injection circuit point 323 and the sense circuit point 327, and a voltage differential of $V_{SR}$ is generated between the sense circuit point 327 and the return circuit point 325. Because the test current ($I_{EST}$) is an AC signal, only the AC component related to $I_{TEST}$ is evaluated, so that any electrode DC offsets are ignored. This removes the effect of any DC offsets $V_I$, $V_S$, and $V_R$ that may be present in the system.

In this example, the ECG acquisition electronics 306 includes differential amplifiers 380 which receive the differential voltages and amplify the signals with a predetermined gain (G1). The amplified signals are then measured by the analog to digital converter 336. The digital data representing the measured amplified differential voltages $V_{IS}$ and $V_{SR}$ is then stored in a computer readable storage device, at least temporarily, by the processing device 328. Further processing 328 is then performed by the processing device 328.

The differential amplifiers 380 are an example of at least part of differential measurement circuitry. In some embodiments the differential measurement circuitry further includes at least an analog to digital converter. Although the gain of these differential amplifiers will typically be greater than unity, it is also possible to determine contact quality if their gain is unity.

Once the differential voltages have been determined, the magnitude of the contact impedances for the injection electrode 352 and the return electrode 356 can be computed by the processing device 328 using Ohm's law, because all other variables in the equations are known. Equations 1 and 2 illustrate Ohm's law for the differential voltages $V_{IS}$ and $V_{SR}$.

$$V_{IS}=(V_I-V_S)+I_{TEST}*(R_{SERIES}+R_{FILTER}+Z_I) \quad \text{Equation 1}$$

$$V_{SR}=(V_S-V_R)+I_{TEST}*(Z_R+R_{SERIES}+R_{FILTER}) \quad \text{Equation 2}$$

Because no test current flows through the sense electrode 354 and the sense lead 364, no voltage drop occurs across the contact impedance $Z_S$ or the associated series resistors, and therefore Equations 1 and 2 do not include contributions from these components.

In embodiments in which the differential voltages are amplified, such as by the differential amplifiers 382 and 384 having a gain of G1, the detected voltages $V_{IS}$ and $V_{SR}$ are multiplied by the known gain (G1), as shown in Equations 3 and 4.

$$\text{Amplified } V_{IS}=G1*((V_I-V_S)+I_{TEST}*(R_{SERIES}+R_{FILTER}+Z_I)) \quad \text{Equation 3:}$$

$$\text{Amplified } V_{SR}=G1*((V_S-V_R)+I_{TEST}*(Z_R+R_{SERIES}+R_{FILTER})) \quad \text{Equation 4:}$$

Therefore, amplified $V_{IS}$, amplified $V_{SR}$, $G_1$, $I_{TEST}$, $R_{FILTER}$, and $R_{SERIES}$ are all known (or measured) values, such that the only remaining variables are the DC offsets ($V_I$, $V_S$, and $V_R$) and the contact impedances $Z_1$ and $Z_R$.

The processing device 328 processes the detected $V_{IS}$ and detected $V_{SR}$ signals. In some embodiments, the processing device 328 performs full wave synchronous detection to determine the peak to peak values of the detected signals. By utilizing the computed peak to peak values, the DC offsets make no net contribution, thereby removing those components from Equations 3 and 4.

In some embodiments, the processing device 328 further filters the signal utilizing an integration operation. The integration operation successively adds the detected peak to peak voltages for each period of the test signal, which averages out the contributions from external sources such as power line frequencies, pacemaker pulses, and the like, because such contributions will not be synchronized with the test signal or the sampling frequencies. Further, if a particular sample is much different than a previous sample (such that it exceeds a predetermined threshold difference value), the processing device 328 can operate to skip a full period of the detected signal from the integration operation to reduce the effects of large voltage spikes that may be present (such as from a pacemaker pulse). Excluding a full period of the test signal rather than just one sample is necessary because peak to peak signal values are required. In this case, the test operation is extended for an equivalent duration (an additional full period of the test signal). This additional filtering operation removes the effect of pacemaker pulses and other potentially large artifacts from the detected results, thereby improving the accuracy of the contact impedance calculations.

The results can then be used by the processing device 328 to compute the contact impedances $Z_I$ and $Z_R$ for the injection electrode 352 and for the return electrode 356. Therefore, with a single test operation, the contact impedances for two individual electrodes 352 and 356 can be simultaneously measured.

In the above discussion, some approximations are made. For example, it is recognized that impedances may include a real component and an imaginary component. Although the above computations could alternatively be performed utilizing both real and imaginary components, it is adequate to simplify the computations to the real components. Also note that for purposes of evaluating electrode contact quality, precise measurements of impedance are not required.

Figure 10:
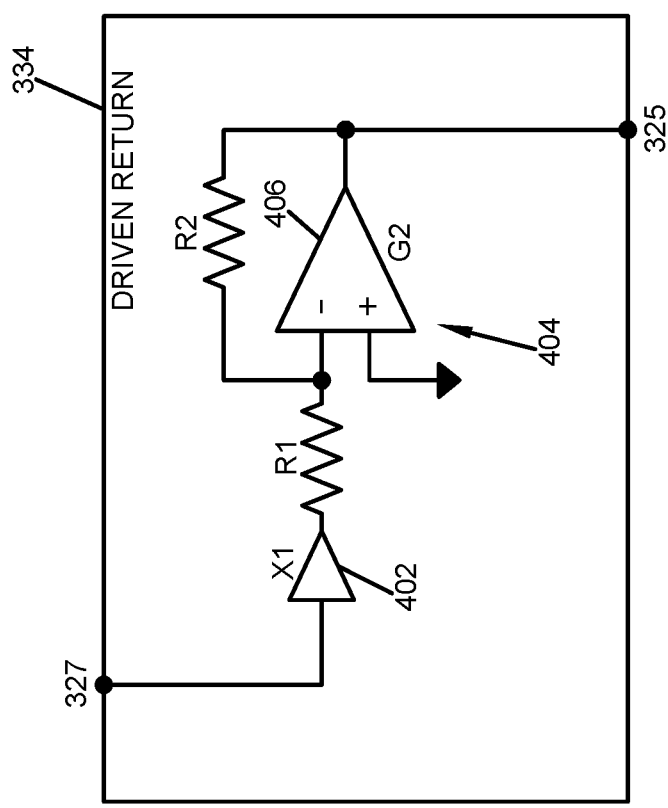
FIG. 10 illustrates a simplified schematic example of driven return circuitry of the electrode contact quality evaluation circuitry shown in FIG. 9.

FIG. 10 illustrates a simplified example of the driven return circuitry 334. In this example, the driven return circuitry 334 includes a buffer 402 and an inverting amplifier 404. An example of the inverting amplifier includes an op amp 406 and resistors R1 and R2 arranged in an inverting amplifier configuration.

The signal from circuit point 327 (FIG. 9) is provided to the buffer 402 and is then inverted and amplified by the inverting amplifier 404. The gain of the inverting amplifier is set by the ratio of R2 to R1 to obtain the appropriate gain. In some embodiments, the gain is in a range from about 10 to about 100. During testing, the signals obtained from the injected electrode are well behaved, and have only small amounts of power line frequency interference. However, it is normal when an ECG device is used in an electrically-noisy environment for the voltage on a driven reference electrode to contain relatively large amounts of power line frequency interference. (This is consistent with the way a driven reference electrode is supposed to work.) Consequently, signals obtained from a reference electrode may be so erratic as to be unusable unless proper processing is used.

Although the term "driven reference electrode" is sometimes used herein, the driven reference electrode also serves as a return path for the injected test current. Accordingly, the terms "driven return electrode" and "return electrode" are sometimes alternatively used herein to refer to the same electrode which serves all of these functions.

To be usable, signals that are obtained from the driven reference electrode must be integrated over longer intervals during the synchronous detection process than for signals obtained from the injected electrode. Ideally, the integration interval for signals obtained from the driven reference electrode should contain whole periods of any expected power line frequency—most particularly of both 60 Hz and 50 Hz. To meet this latter condition requires using integration intervals that are integer multiples of 100 milliseconds.

Although using such integration intervals removes most power line frequency interference from the integrated measurements, it cannot always sufficiently reject artifact from implanted pacemakers. The processing technique of excluding samples that deviate from the average by more than a certain amount works quite well for removing pacemaker pulse artifact from signals obtained from an injected electrode, but a great percentage of the samples obtained from a driven electrode inherently deviate excessively from its average. The simplest and perhaps the only effective way of removing pacemaker pulse artifact from signals obtained from the driven electrode is averaging over a sufficiently long interval, e.g. at least several tenths of a second.

Figure 11:
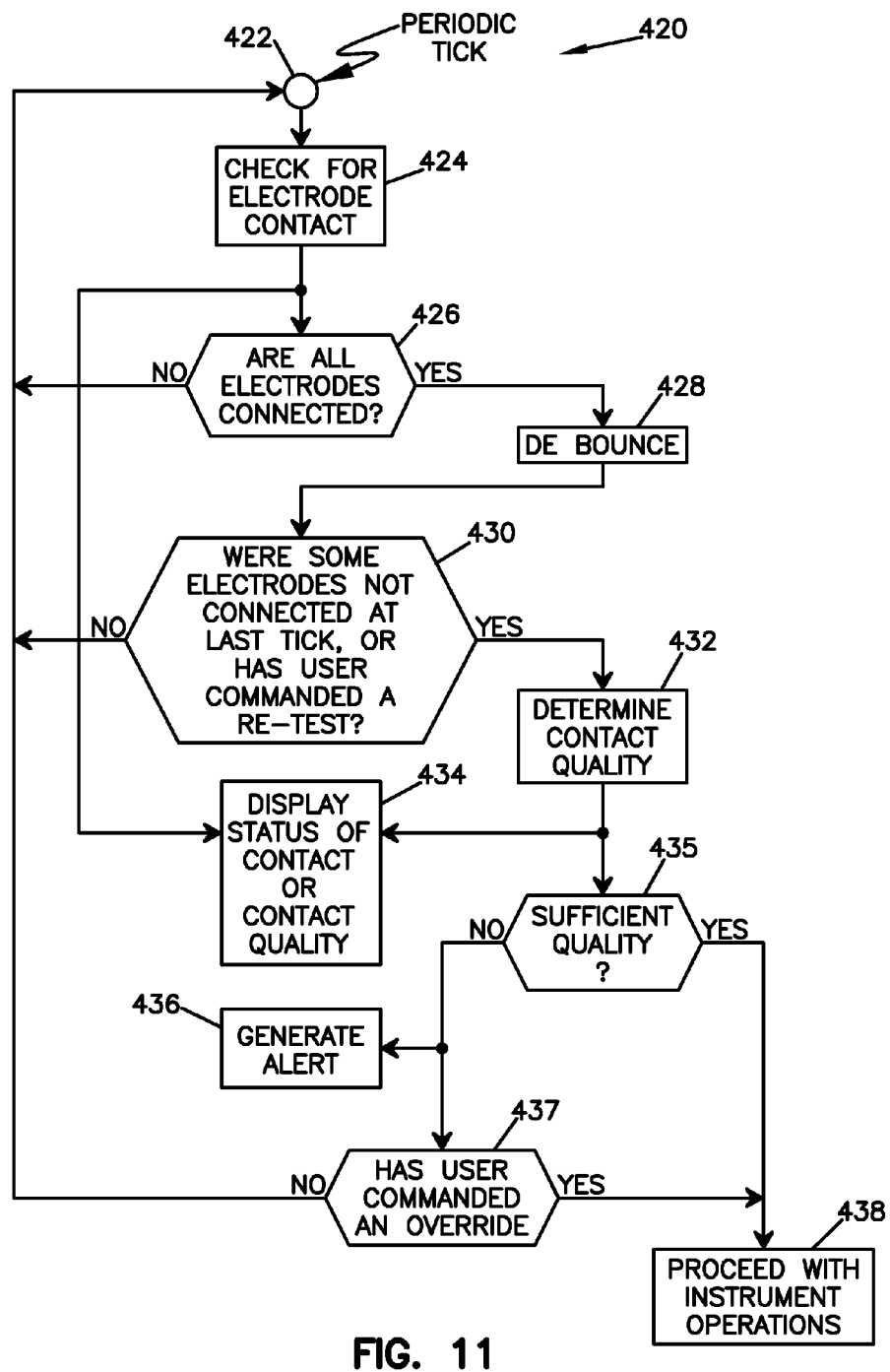
FIG. 11 is a flow chart illustrating an example method of operating an instrument using surface contact electrodes.

FIG. 11 is a flow chart illustrating an example method 420 of operating an instrument 100 using surface contact electrodes. In this example, method 420 includes operations 422, 424, 426, 428, 430, 432, 434, 435, 436, and 438.

The operation 422 generates a periodic timing tick, in order to repetitively trigger checking for any lead off conditions. The timing of these ticks is a compromise between response time for detecting when a lead is connected or disconnected versus the processing burden consumed by the testing.

The operation 424 is performed to detect the connection of the electrodes. While performing the operation 424, the instrument operates in an electrode connection detection mode. In some embodiments, the operation 424 is performed by the electrode contact detection circuitry 302, shown in FIG. 7.

In some embodiments, a visual indication is presented by the instrument 100 to identify those electrodes that are determined to be connected. For example, a light or graphical element is illuminated on the display device 246 of the lead interface unit 108 (FIG. 8), and/or on the display device 132 of the base unit 102 (FIG. 3), as the connection of each electrode is detected. This operation 434 provides a visual indication to the user that the instrument 100 has detected the connection of the electrode or set of electrodes.

The operation 426 is performed to determine whether the electrodes are connected. In some embodiments, the operation 426 waits for all electrodes to be connected before proceeding with the subsequent operations. In other embodiments, the operation 426 waits for at least a subset of the electrodes (e.g., at least three electrodes) to be connected before proceeding with subsequent operations. In some embodiments, the operation requires only three or more electrodes be connected in order to proceed to subsequent operations.

In some embodiments, the debounce operation 428 is included to prevent unintentional startups of determining contact quality because of transient behavior of the output state of the operation 426. For example, such transients may occur when a patient is defibrillated while connected to instrument 100.

In some embodiments, it is desirable to automatically trigger testing of contact quality after the last electrode or the last electrode of a defined subset of electrodes is connected to the patient. Furthermore it is desirable in some embodiments to allow the user to manually command a repeat of the contact quality testing when desired e.g., after the electrodes have been in place for a long time and their contact quality may be suspect. Operation 430 provides these control actions. Alternatively, an automatic re-test may be triggered periodically.

Once the appropriate number of electrodes are determined to have been connected, the operation 432 is performed to determine the quality of the electrode connections. For example, in some embodiments the instrument 100 determines the contact impedances of each of the connected electrodes, such as illustrated and described with reference to FIG. 12. In some embodiments the instrument 100 determines a quality level of the electrode connections, such as illustrated and described with reference to FIG. 13. One example of electrode quality levels include "good," "fair," and "poor." Further, in some embodiments the instrument 100 generates visual indications of the electrode contact quality levels, such as illustrated and described with reference to FIGS. 14 and 15. Still other embodiments use numbers to offer greater resolution for contact quality, e.g. where 1 is best and 10 is too poor to use.

In some embodiments, a visual indication is presented by the instrument 100 to identify the contact quality of those electrodes that are determined to be connected. For example, a light or graphical element is illuminated on the display device 246 of the lead interface unit 108 (FIG. 8), and/or on the display device 132 of the base unit 102 (FIG. 3), as the connection of each electrode is detected. This operation 434 provides a visual indication to the user of the contact quality of each connected electrode.

The operation 435 is performed to determine if the electrode contact quality level is of sufficient quality. In some embodiments, each of the determined electrode contact impedances is compared with a predetermined maximum acceptable electrode contact impedance. If any of the determined electrode contact impedances exceed the maximum acceptable electrode contact impedance, the corresponding electrodes are determined to have insufficient electrode contact quality.

In another example embodiment, the determined electrode contact quality levels are evaluated to determine whether they are of sufficient quality. As one example, electrode contact quality levels of "good" and "fair" are determined to be of sufficient quality, while a contact quality level of "poor" is determined to be of insufficient quality.

Figure 15:
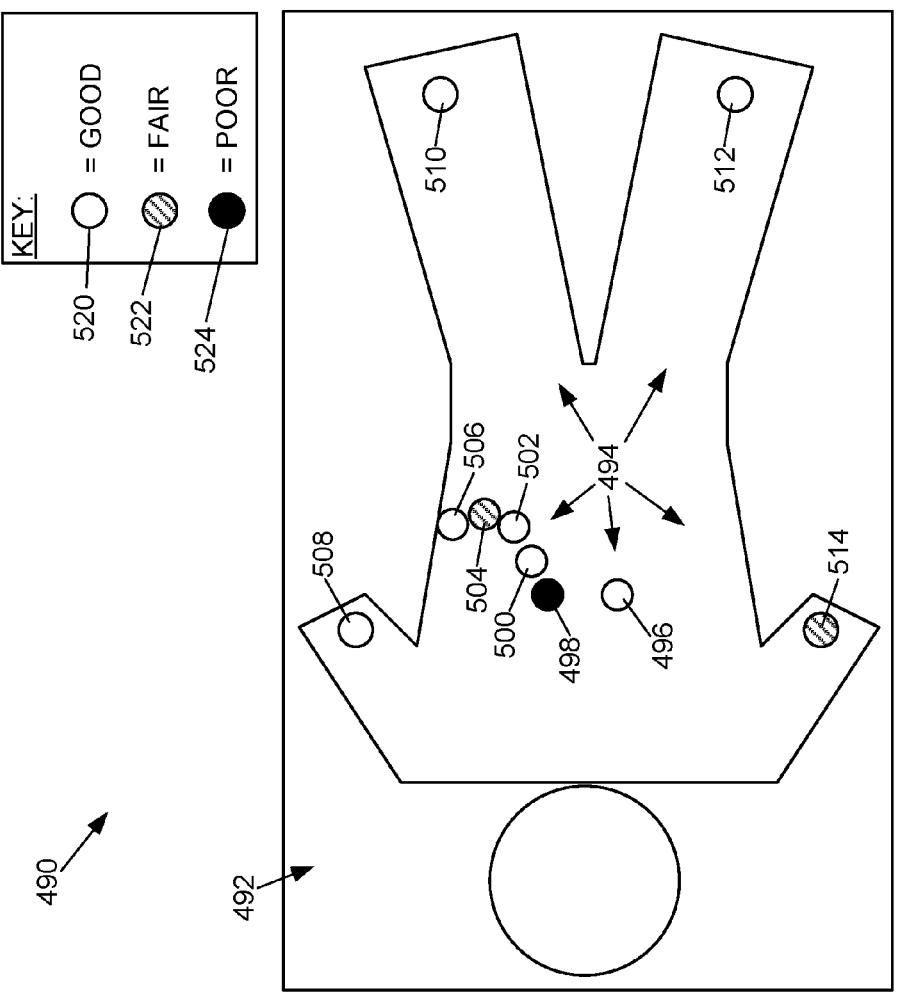
FIG. 15 is a diagram illustrating an example display showing the electrode contact quality levels.

If one or more electrodes are determined to have insufficient electrode contact quality, the operation 436 is performed to generate an alert. An example of an alert is a visual indication, such as shown in FIG. 15. Such a visual indication may be displayed on a user interface, such as on the display device 246 of the lead interface unit 108 (FIG. 8), and/or on the display device 132 of the base unit 102 (FIG. 3). The message informs the user that at least one of the electrodes is not adequately connected to the patient, and may instruct the user to reconnect one or more of the electrodes, for example. In some embodiments, the alert identifies the one or more electrodes that are not adequately connected. Another example of an alert is an audible alert, such as a beep, or other audible sound. Other embodiments utilize other alerts or combinations of alerts.

In some embodiments, operation 435 inhibits normal instrument operation until the quality of the electrode connections are determined to be sufficiently high. In another possible embodiment, the instrument includes an override mode 437. Upon receiving an input from the user indicating a desire to proceed with instrument operation despite the insufficient quality of the connection of one or more electrodes, the method 420 proceeds to the operation 438.

If all electrodes are determined to have sufficient quality or an override command 437 is received, the operation 438 is performed to proceed with normal instrument operation. For example, when the instrument 100 is an ECG instrument, the operation 438 proceeds to monitor electrical signals from the heart using the electrodes.

Figure 12:
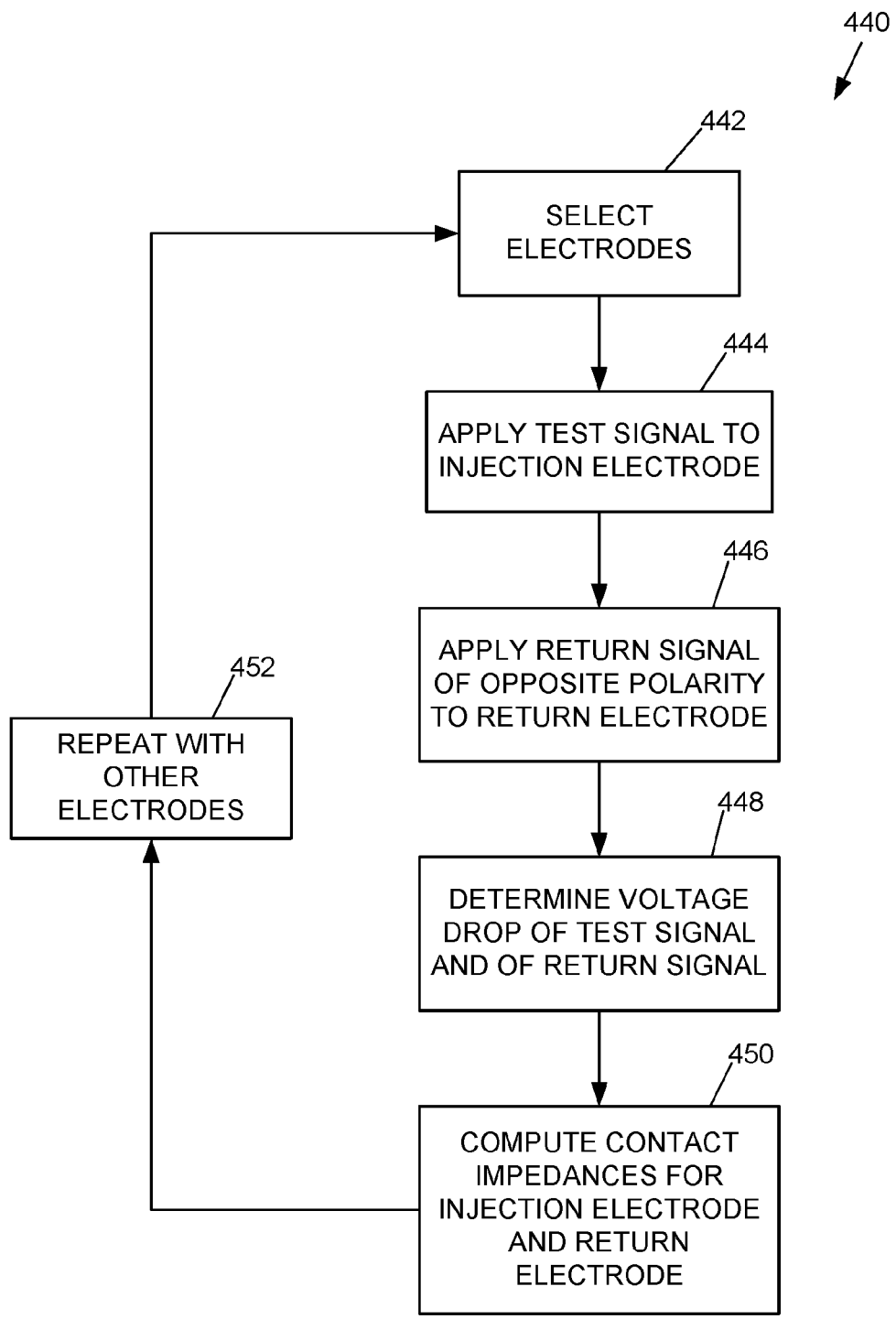
FIG. 12 is a flow chart illustrating an example method of determining electrode contact impedances.

FIG. 12 is a flow chart illustrating an example method 440 of determining electrode contact impedances. In some embodiments, the method 440 is an example of part or all of the operation 432, shown in FIG. 11, which operates to determine the quality of electrode connections. In this example, method 440 includes operations 442, 444, 446, 448, 450, and 452.

The operation 442 selects at least three electrodes from the complete set of electrodes. In some embodiments, the operation 442 involves the selection of an electrode as an injection electrode, one or the average of two or more other electrodes as a sense electrode, and a third electrode as a return electrode, where the method 440 is then performed to determine the contact impedances for the electrodes selected as the injection electrode and the return electrode. In some embodiments, once the electrodes have been selected, signals are generated to control the injection, return, and sense electrode selection circuitry 322, 324, and 326 (shown in FIG. 8) to make the appropriate selections.

The operation 444 involves applying a test signal to the injection electrode. Examples of the test signal are described herein. In some embodiments, operation 444 is performed by the test current source 332 (shown in FIGS. 8 and 9).

The operation 446 generates a return signal of opposite polarity and applies that signal to the return electrode. In some embodiments, operation 446 is performed by the driven return circuitry 334 (shown in FIGS. 8-10).

The operation 448 determines the voltage drop of the test signal and the return signal. In some embodiments, operation 448 involves determining the voltage drop between the test current source and the sense electrode 354 (FIG. 9). In another embodiment, the voltage drop is the differential voltage $V_{IS}$ across circuit points 323 and 327 (FIG. 9).

In some embodiments, operation 448 also involves determining the voltage drop between the driven return circuitry 334 and the sense electrode 354 (FIG. 9). In another embodiment, the voltage drop is the differential voltage $V_{SR}$ across circuit points 327 and 325 (FIG. 9).

In some embodiments, the differential voltages are amplified prior to measurement.

The operation 450 is then performed to compute contact impedances for the injection electrode and the return electrode using the voltage drops determined in operation 448.

Operation 452 is then performed to repeat the operations 442, 444, 446, 448, and 450 with at least one different electrode. The process can be repeated until the contact impedances of all electrodes have been determined.

Figure 13:
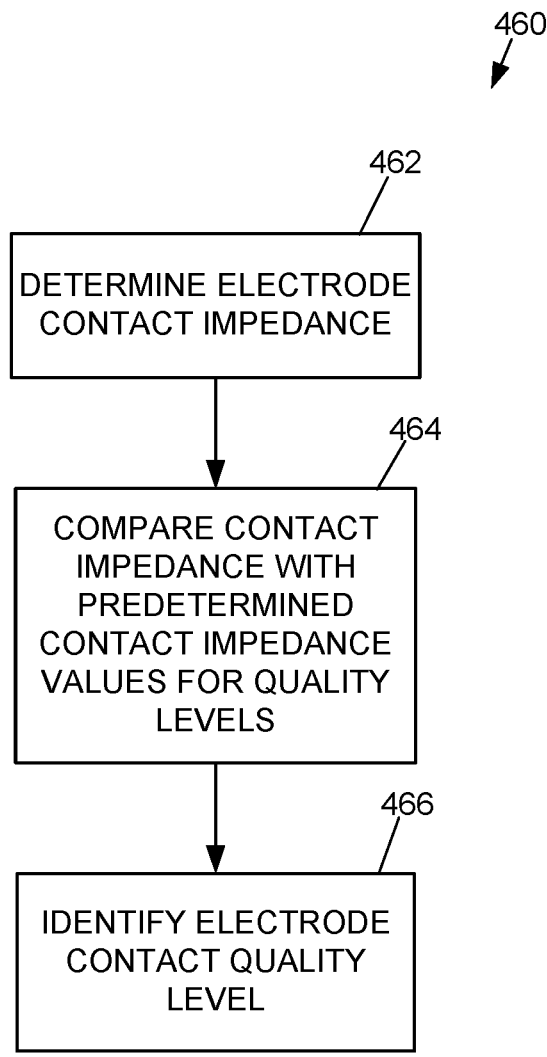
FIG. 13 is a flow chart illustrating an example method of determining an electrode contact quality level.

FIG. 13 is a flow chart illustrating an example method 460 of determining an electrode contact quality level. In some embodiments the method 460 is at least part of the operations 432 or 435, shown in FIG. 11. In this example, method 460 includes operations 462, 464, and 466.

The operation 462 is performed to determine electrode contact impedances. An example of operation 462 is method 440, shown in FIG. 12.

Operation 464 is then performed to compare the electrode contact impedances with predetermined contact impedance values for various quality levels. In some embodiments the operation 464 involves looking up the electrode contact impedance for an electrode in a lookup table. An example of a lookup table is shown in Table 1.

TABLE 1

| Contact Impedance (X) | Electrode Contact Quality Level |
|---|---|
| X <= 10K ohms | Good |
| 10K ohms < X <= 80K ohms | Fair |
| 80K ohms < X <= 120K ohms | Poor |
| X > 120K ohms | Disconnected |

Note that contact impedances are to a first order inversely proportional to the frequency of the test signal. Therefore, the values in a lookup table that is appropriate for one embodiment may not be appropriate for use with an embodiment that uses a different test frequency.

The operation 466 is then performed to identify an electrode contact quality level for the electrode. For example, if an electrode contact impedance is determined to be 8K ohms, Table 1 is used to identify the contact quality level as "good." If an electrode contact impedance is determined to be 25K ohms, Table 1 is used to identify the contact quality level as "fair."

Figure 14:
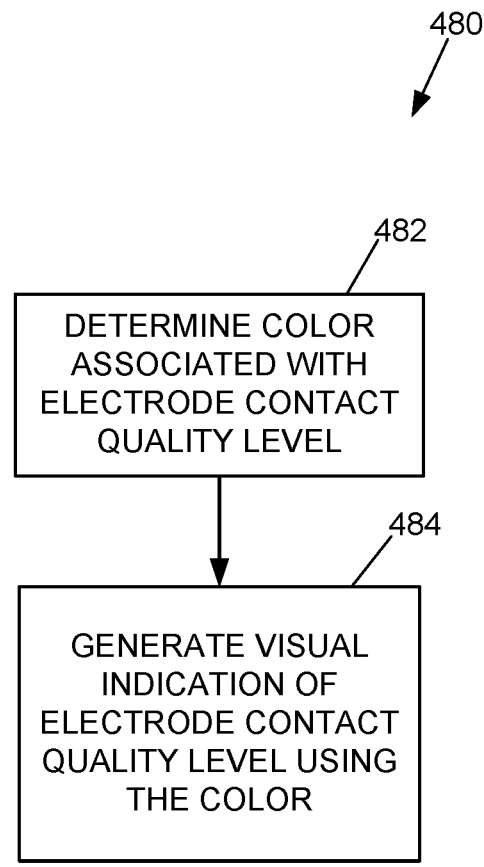
FIG. 14 is a flow chart illustrating an example method of generating a visual indication of an electrode contact quality level.

FIG. 14 is a flow chart illustrating an example method 480 of generating a visual indication of the electrode contact quality level. In this example, the method 480 includes operations 482 and 484.

After an electrode contact quality level has been determined, such as through the method 460, shown in FIG. 13, operation 482 is performed to determine a color associated with an electrode contact quality level. In some embodiments, the color is determined from a lookup table, such as the example shown in Table 2.

TABLE 2

| Electrode Contact Quality Level | Color |
|---|---|
| Good | First Color (Green) |
| Fair | Second Color (Yellow) |
| Poor | Third Color (Off or Flashing Yellow) |
| Disconnected | None |

The operation 484 is then performed to generate a visual indication of the electrode contact quality level using the color. An example is illustrated in FIG. 15.

FIG. 15 is a diagram illustrating an example display 490 showing electrode contact quality levels.

In some embodiments, the display 490 is generated by the instrument 100 to convey to the user information regarding the determined electrode contact quality levels for each of the electrodes. In this example, the display 490 includes a graphical representation of a person 492, and graphical elements 494 representing each of the electrodes. The graphical elements 494 include graphical elements 496, 498, 500, 502, 504, 506, 508, 510, 512, and 514.

In some embodiments, the display 490 is generated by the display device 246 of the lead interface unit 108 (FIG. 8). In another embodiment, the display 490 is generated by the display device 132 of the base unit 102 (FIG. 3). In still other embodiments, display 490 may be generated on both the base unit 102 and the lead interface unit 108.

The graphical representation of the person 492 can be generated and displayed on a display device, such as by illuminating pixels on an LCD display or other type of flat panel display. In another embodiment, the graphical representation can be physically printed, imprinted, molded, or otherwise formed on a housing or other portion of the instrument 100.

The graphical elements 494 convey the electrode contact quality level for each electrode to the user, such as by using different colors for different quality levels. In some embodiments the graphical elements 494 are generated and displayed on a display device, such as by illuminating pixels on an LCD or other type of flat panel display. In another possible embodiment, the graphical elements 494 are LED's, such as multi-color LED's that can be selectively illuminated to generate different colored outputs.

In some embodiments, the graphical elements 494 include only a single color. For example, the graphical element 494 is illuminated when the electrode contact quality level is sufficient and is off when the quality level is insufficient. As another example, the graphical element 494 is illuminated when the electrode contact quality level is insufficient and is off when the quality level is sufficient.

In other embodiments, the graphical elements 494 include multiple colors, such as illustrated in FIG. 15. In this example, the graphical elements 494 include at least three colors. A first color 520 (e.g., green) represents a good quality level. A second color 522 (e.g., yellow) represents a fair quality level. A third color 524 (e.g., black or off) represents a poor quality level. The graphical element 494 being off indicates that the electrode is disconnected.

In this example, most of the electrodes have been determined to have a good electrode contact quality level, including the electrodes represented by graphical elements 496, 500, 502, 506, 508, 510, and 512, and are therefore displayed with the first color. The electrodes represented by graphical elements 504 and 514 were determined to have fair, but lower, quality electrode contact quality levels, and are therefore displayed with the second color. The electrode represented by graphical element 498, however, was determined to have a poor electrode contact quality level, and is therefore displayed with the third color.

Various other visual representations of electrode contact quality levels, including the addition of blinking presentation, or of the electrode contact impedance values themselves, can be provided in other embodiments.

In addition to conveying information regarding electrode contact quality to the user, such information can also be stored and/or transmitted for subsequent use. For example, a log can be maintained identifying electrode contact quality levels that were detected, along with the date and time in which the contact quality evaluation was performed. This can be helpful, for example, for subsequent troubleshooting and for evaluating the operation of the instrument 100.

The various embodiments described above are provided by way of illustration only and should not be construed to limit the claims attached hereto. Those skilled in the art will readily recognize various modifications and changes that may be made without following the example embodiments and applications illustrated and described herein, and without departing from the true spirit and scope of the following claims.

What is claimed is:

1. A system comprising:
    an injection, a sense and a return skin-contacting electrode;
    a current source, wherein the current source applies an AC test current to the injection skin-contacting electrode, the AC test current having a first polarity and a first magnitude,
    a driven return coupled between the sense skin-contacting electrode and the return skin-contacting electrode, wherein the driven return accepts a return of the AC test current through the return skin-contacting electrode, wherein the driven return operates to keep a voltage at the sense skin contacting electrode centered at an isolated ground potential, and wherein the driven return generates a return current that is supplied to the injection skin-contacting electrode, the return current having a polarity opposite to the first polarity;

a processor, the processor executing instructions for performance of a simultaneous test to determine the quality of skin contact of both the injection and return skin-contacting electrodes, wherein execution of the instructions cause the processor to:

determine both a first differential voltage between the injection and sense skin-contacting electrodes and a second differential voltage between the sense and return skin-contacting electrodes after application of the AC test current and the return current; and determine a first and second magnitude of a contact impedance for each of the injection and return skin-contacting electrodes, respectively, based on the first and second differential voltages, wherein the first and second magnitudes of contact impedance are representative of a quality of skin contact of the injection and return skin-contacting electrodes, respectively.

2. The system of claim 1, wherein the processor is further caused to prevent use of the injection and/or return skin-contacting electrode in a patient-based measurement of electrical activity when the impedance of the injection and/or return skin-contacting electrode exceed a threshold impedance.

3. The system of claim 2, wherein the patient-based measurement of electrical activity comprises: an electrocardiograph (ECG), an electroencephalograph (EEG), or an electromyography (EMG).

* * * * *